(12) United States Patent
Khajavi

(10) Patent No.: US 9,721,064 B2
(45) Date of Patent: Aug. 1, 2017

(54) SYSTEM AND METHOD FOR PREVENTING WRONG-SITE SURGERIES

(71) Applicant: StartBox, LLC, Atlanta, GA (US)

(72) Inventor: Kaveh Khajavi, Atlanta, GA (US)

(73) Assignee: StartBox, LLC, Atlanta, GA (US)

( * ) Notice: Subject to any disclaimer, the term of this patent is extended or adjusted under 35 U.S.C. 154(b) by 0 days.

(21) Appl. No.: 14/873,974

(22) Filed: Oct. 2, 2015

(65) Prior Publication Data

US 2016/0022361 A1     Jan. 28, 2016

Related U.S. Application Data

(63) Continuation-in-part of application No. 14/143,920, filed on Dec. 30, 2013, now Pat. No. 9,168,107,
(Continued)

(51) Int. Cl.
    *G06F 19/00*        (2011.01)
    *A61B 90/96*        (2016.01)
    (Continued)

(52) U.S. Cl.
    CPC .............. *G06F 19/34* (2013.01); *A61B 34/25* (2016.02); *A61B 90/90* (2016.02); *A61B 90/96* (2016.02);
    (Continued)

(58) Field of Classification Search
    CPC ... A61B 90/90; A61B 90/96; A61B 2034/252; A61B 34/25; A61B 2034/254; G06F 19/327; G06F 19/34
    See application file for complete search history.

(56) References Cited

U.S. PATENT DOCUMENTS

| | | |
|---|---|---|
| 1,625,035 A | 4/1927 | Lilly |
| 3,391,694 A | 7/1968 | Spaeth |
| (Continued) | | |

FOREIGN PATENT DOCUMENTS

| | | |
|---|---|---|
| WO | WO9424021 | 10/1994 |
| WO | WO9631414 | 10/1996 |
| (Continued) | | |

OTHER PUBLICATIONS

Wong, D., MD, et al, "NASS endorses JCAHO universal protocol: Guidelines for implementing the Universal Protocol for Preventing Wrong Site, Wrong Procedure and Wrong Person Surgery", North American Spine Society, pp. 21-24, (Mar.-Apr. 2004).
(Continued)

*Primary Examiner* — Howie Matthews
(74) *Attorney, Agent, or Firm* — Meunier Carlin & Curfman LLC

(57) ABSTRACT

A container holds at least one surgical implement, has a lock mechanism, and has a signature label that impedes access to the surgical implement until the correct surgical site is confirmed. A method of using the container includes the steps of confirming the correct surgical site, signing the label and removing it from the container, placing the label in the medical record, unlocking the container, removing the implement, and beginning the surgery, wherein the surgical team is forced to pause to confirm the correct surgical site before starting the surgery. The system and method may also include a wrong site surgery profile used by individuals within the surgical procedure environment and third parties for tracking and determining if, and where, a wrong site surgical procedure occurred. The profile can be updated, tacked and monitored while a patient is interacting within the medical environment.

20 Claims, 30 Drawing Sheets

Related U.S. Application Data which is a continuation-in-part of application No. 11/270,686, filed on Nov. 9, 2005, now Pat. No. 8,616,215.

(60) Provisional application No. 60/626,240, filed on Nov. 9, 2004.

(51) Int. Cl.
| | |
|---|---|
| *A61B 90/90* | (2016.01) |
| *A61B 34/00* | (2016.01) |
| *A61B 17/06* | (2006.01) |
| *A61M 5/00* | (2006.01) |
| *A61B 17/3217* | (2006.01) |
| *A61M 5/32* | (2006.01) |
| *A61M 19/00* | (2006.01) |
| *A61B 50/00* | (2016.01) |
| *A61B 50/31* | (2016.01) |
| *A61B 50/30* | (2016.01) |
| *A61B 50/33* | (2016.01) |
| *A61B 50/36* | (2016.01) |
| *A61B 90/92* | (2016.01) |
| *A61B 90/98* | (2016.01) |
| *A61B 90/00* | (2016.01) |

(52) U.S. Cl.
CPC ...... *G06F 19/327* (2013.01); *A61B 17/06114* (2013.01); *A61B 17/3217* (2013.01); *A61B 50/30* (2016.02); *A61B 50/3001* (2016.02); *A61B 50/31* (2016.02); *A61B 50/33* (2016.02); *A61B 50/362* (2016.02); *A61B 90/92* (2016.02); *A61B 90/98* (2016.02); *A61B 2034/254* (2016.02); *A61B 2050/008* (2016.02); *A61B 2050/0059* (2016.02); *A61B 2050/3008* (2016.02); *A61B 2090/0807* (2016.02); *A61B 2090/08021* (2016.02); *A61B 2090/395* (2016.02); *A61M 5/002* (2013.01); *A61M 5/3205* (2013.01); *A61M 19/00* (2013.01); *A61M 2209/06* (2013.01)

(56) References Cited

U.S. PATENT DOCUMENTS

| | | | |
|---|---|---|---|
| 3,497,982 | A | 3/1970 | Schulz |
| 3,517,636 | A | 6/1970 | Colon-Morales |
| 3,627,122 | A | 12/1971 | Garbe, Jr. |
| 3,698,383 | A | 10/1972 | Baucom |
| 3,727,749 | A | 4/1973 | Martin |
| 3,831,625 | A | 8/1974 | Roediger |
| 4,243,140 | A | 1/1981 | Thrun |
| 4,373,629 | A | 2/1983 | Ulin et al. |
| 4,476,381 | A | 10/1984 | Rubin |
| 4,620,644 | A | 11/1986 | Miller |
| 4,736,844 | A | 4/1988 | Scott et al. |
| 4,848,587 | A | 7/1989 | Nipp |
| 4,944,603 | A | 7/1990 | Cornish et al. |
| 4,979,616 | A | 12/1990 | Clanton |
| 4,988,062 | A | 1/1991 | London |
| 5,000,484 | A | 3/1991 | Phelan et al. |
| 5,024,326 | A | 6/1991 | Sandel et al. |
| 5,031,768 | A | 7/1991 | Fischer |
| 5,067,612 | A | 11/1991 | Tsuchiya et al. |
| 5,167,193 | A | 12/1992 | Withers et al. |
| 5,181,609 | A | 1/1993 | Spielmann et al. |
| 5,193,678 | A | 3/1993 | Janocik et al. |
| 5,195,538 | A | 3/1993 | Eldridge, Jr. et al. |
| 5,199,567 | A | 4/1993 | Discko, Jr. |
| 5,225,162 | A | 7/1993 | Scoville |
| 5,227,765 | A | 7/1993 | Ishizuka et al. |
| 5,293,990 | A | 3/1994 | Masakayan |
| 5,318,543 | A | 6/1994 | Ross et al. |
| 5,338,123 | A | 8/1994 | Obersteller et al. |
| 5,339,955 | A | 8/1994 | Horan et al. |
| 5,356,006 | A | 10/1994 | Alpern et al. |
| 5,381,487 | A | 1/1995 | Shamos |
| 5,394,982 | A | 3/1995 | Sawaya |
| 5,538,132 | A | 7/1996 | Propp et al. |
| D374,282 | S | 10/1996 | Hoftman |
| 5,566,828 | A | 10/1996 | Claes et al. |
| 5,741,301 | A | 4/1998 | Pagedas |
| 5,762,255 | A | 6/1998 | Chrisman et al. |
| 5,799,788 | A | 9/1998 | Webb |
| 5,824,068 | A | 10/1998 | Bugge |
| 5,829,788 | A | 11/1998 | Jackson |
| 5,938,063 | A | 8/1999 | Hoftman |
| 5,951,160 | A | 9/1999 | Ronk |
| 5,976,014 | A | 11/1999 | Petrick et al. |
| 5,984,931 | A | 11/1999 | Greenfield |
| 6,056,737 | A | 5/2000 | Rosen |
| 6,158,437 | A | 12/2000 | Vagley |
| 6,247,592 | B1 | 6/2001 | Racicot et al. |
| 6,343,695 | B1 | 2/2002 | Petrick et al. |
| 6,364,096 | B1 | 4/2002 | De Baets et al. |
| 6,685,017 | B2 | 2/2004 | Erickson |
| 6,923,319 | B1 | 8/2005 | Erickson et al. |
| 7,032,752 | B2 | 4/2006 | Krackow |
| 7,297,148 | B2 | 11/2007 | Waxman |
| 7,389,928 | B2 | 6/2008 | Lubow |
| 7,635,348 | B2 | 12/2009 | Raven et al. |
| 2002/0014029 | A1 | 2/2002 | Copelan |
| 2002/0179094 | A1 | 12/2002 | Perlow |
| 2003/0111361 | A1 | 6/2003 | Fischer et al. |
| 2003/0182815 | A1 | 10/2003 | Carlson, II |
| 2003/0184081 | A1 | 10/2003 | Carlson, II |
| 2003/0187458 | A1 | 10/2003 | Carlson, II |
| 2004/0031708 | A1 | 2/2004 | Spagna |
| 2004/0033327 | A1 | 2/2004 | Marks, III et al. |
| 2004/0056478 | A1 | 3/2004 | Bruce |
| 2004/0069667 | A1 | 4/2004 | Tomellini et al. |
| 2004/0116907 | A1 | 6/2004 | Tartaglia |
| 2004/0118410 | A1 | 6/2004 | Griesbach et al. |
| 2004/0128892 | A1 | 7/2004 | Valenti, Jr. |
| 2004/0163982 | A1 | 8/2004 | Wilkinson et al. |
| 2004/0236871 | A1 | 11/2004 | Waxman |
| 2004/0261644 | A1 | 12/2004 | Stewart et al. |
| 2005/0029145 | A1 | 2/2005 | Krackow |
| 2005/0038407 | A1 | 2/2005 | Sumka |
| 2005/0045503 | A1 | 3/2005 | Wong et al. |
| 2005/0183182 | A1 | 8/2005 | Keenan |
| 2006/0042977 | A1 | 3/2006 | Sandel |
| 2006/0096877 | A1 | 5/2006 | Khajavi et al. |
| 2006/0124493 | A1 | 6/2006 | Krackow |
| 2006/0145871 | A1 | 7/2006 | Donati et al. |
| 2006/0149296 | A1 | 7/2006 | Stanners |
| 2006/0169154 | A1 | 8/2006 | Nelson |
| 2008/0077444 | A1 | 3/2008 | MacLeod |
| 2009/0178685 | A1 | 7/2009 | Haines et al. |
| 2011/0250104 | A1 | 10/2011 | Martel et al. |

FOREIGN PATENT DOCUMENTS

| | | |
|---|---|---|
| WO | WO2006053005 | 5/2006 |
| WO | WO2007000639 | 1/2007 |
| WO | WO2009003231 | 1/2009 |

OTHER PUBLICATIONS

Healy, G., MD, et al, "Error reduction through team leadership: Applying aviation's CRM model in the OR", Bulletin of the American College of Surgeons, vol. 91, No. 1, 6 pgs, (Feb. 2006).

Sentinel Event Statistics, 1 page, (Dec. 31, 2005).

Anonymous, "Wrong site surgery", American Academy of Orthopaedic Surgeons, Internet article, http://www5,aasos.org/wrong/viewscrp.cfm, (Retrieved Feb. 26, 2009).

Cash, A., RN, "Wrong site surgery", Nursing Risk Management, Dept. of Legal Medicine, 15 pgs., (2003).

Anonymous, "A Follow-up Review of Wrong Site Surgery", Joint Commission on Accreditation of Healthcare Organizations, Sentinel Events Alert, www.jcaho.org, Issue 24, 4 pgs, (Dec. 5, 2001).

(56) References Cited

OTHER PUBLICATIONS

Cowell, H. MD, "Wrong-Site Surgery: Editorial", vol. 80-A, No. 4, The Journal of Bone and Joint Surgery, Inc., (Apr. 1998).
Seiden, S. MD, et al, "Wrong-Side/Wrong-Site, Wrong-Procedure, and Wrong-Patient Adverse Events", Arch. Surg. vol. 141, pp. 931-939, Internet article retrieved Feb. 12, 2009: http://www.archsurg.ama-assn.org/cgi/content/full141/9/931#REF-SOA6 . . . , (Sep. 2006).
Davis, R., "Wrong-Site Surgeries on the Rise", USA Today, Internet article retrieved Feb. 7, 2009: http://www.usatoday.com/news/health/206-04-17-wrong-surgery_x.htm, (Apr. 17, 2006).
Clark, J. MD, et al, "Getting Surgery Right CME", Annals of Surgery, Medscape LLC, 23 pgs., (Nov. 16, 2007).
Kwann, M. MD, et al, "Incidence, Patterns and Prevention of Wrong-Site Surgery", Arch. Surg., http://www.archsurg.com, American Medical Assn, vol. 141, pp. 353-358, (Apr. 2006).
Blumenstyk, G., "A System to Prevent 'Wrong-Site Surgery'", Internet article: http://www.chronicle.com, 52:24: A35-36, (Feb. 17, 2006).
Phurrough, S. MD, et al, "Coverage Decision Memorandum for a Surgical or Other Invasive Procedure Performed on the Wrong Patient", Decision Memo for Surgery on the Wrong Patient CAG-00403N, 8 pgs., (Jan. 15, 2009).
Phurrough, S. MD, et al, "Coverage Decision Memorandum for a Surgical or Other Invasive Procedure Performed on the Wrong Patient" Decision Memo for Wrong Surgery Performed on a Patient CAG-00401N, 9 pgs, (Jan. 15, 2009).
Phurrough, S. MD, et al, "Coverage Decision Memorandum for a Surgical or Other Invasive Procedure Performed on the Wrong Patient" Decision Memo for Wrong Surgery Performed on a PatientCAG-00402N, 9 pgs, (Jan. 15, 2009).
Reinberg, S., "Surgeon's Checklist Saves Lives", The Washington Post, Scout News, LLC, Internet article retrieved Feb. 18, 2009: http:www.washingtonpost.com/wp-dyn/content/article/2009/01/14 . . . , 2 pgs., (Jan. 14, 2009).
Meinberg, E. et al, "Incidence of Wrong-Site Surgery Among Hand Surgeons", Journal Bone and Joint Surgery, www.jbjs.org, Internet article: http:www.ejbjs.org/cgi/content/full/85/2/193/DC1, 6 pgs., Needham, MA, (Feb. 12, 2009).
The Joint Commission, Sentinel Event Statistics, Internet article retrieved Feb. 12, 2009: http://www.jointcommission.org/SentinelEvents/Statistics, (Dec. 31, 2008).
The Joint Commission, "Lessons Learned: Wrong Site Surgery", Sentinel Event Alert, Internet article retrieved Feb. 26, 2009: http://www.jointcommission.org/SentinelEvents/Statistics, 1 page.
Joint Commission on Accreditation of Healthcare Organizations. Sentinel Events: Approaches to Error Reduction and Prevention; vol. 24, No. 4; 13 pgs.
Zeal, A., MD, "Error Results in Doctor's Paradigm Shift", vol. 14, No. 4, AANS Bulletin 27, 3 pgs.
Berwick, D. et al., "Sentinel Events: Approaches to error reduction and prevention", Joint Commissions on Accreditation of Healthcare Organizations, Journal on Quality Improvement, vol. 24, No. 4, pp. 175-186.
Sandel Medical Industries, LLC., "Time Out Safety Kit", Internet article: http//www.sandelmedical.com/productsdetail.aspx?id=26.
The Joint Commission, "Reducing the Risk of Wrong Site Surgery", Internet article: http://www.centerfortransforminghealthcare.org/UserFiles/file/CT-H.sub.--WSS.sub.--Storyboard.sub.--final.sub.--2011.pdf, 23 pgs., (2011).
International Preliminary Report on Patentability dated Jul. 5, 2016, received in connection with International application No. PCT/US2014/072780.
DeVine, J., MD et al, "Avoiding Wrong Site Surgery: A Systematic Review", SPINE, 2010, vol. 35, No. 9S, pp. S28-S36.
Catchpole, K. et al., "The problem with checklists", BMJ Qual Saf, Jun. 2015, vol. 24, pp. 545-549.

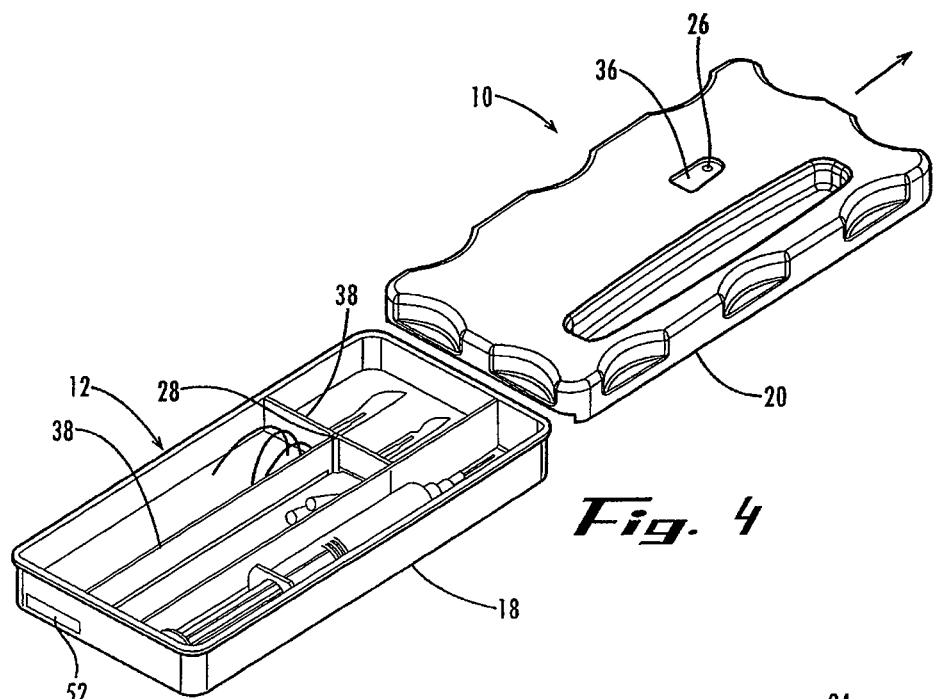
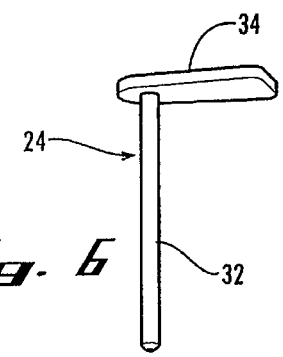
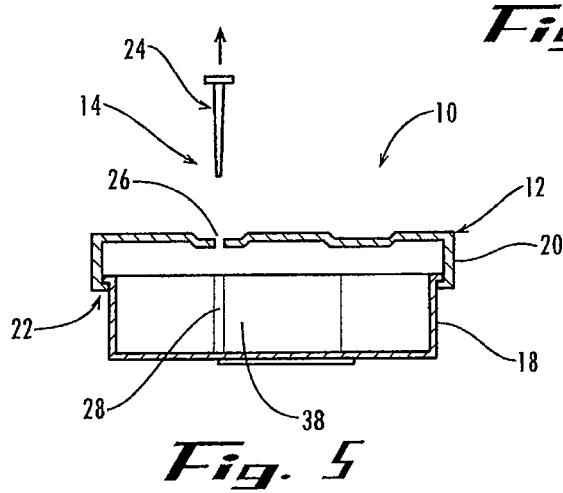

REMOVE LABEL A TO ACCESS SURGICAL PEN.
SIGN AND REMOVE LABEL B TO OPEN SURGICAL TRAY.

Fig. 7 — 40

CONFIRMATION & SIGNATURES/LABEL B

PATIENT NAME: _____

OPERATIVE SITE/SURGICAL PROCEDURE: ___ _____

NECESSARY IMPLANTS AND/OR INSTRUMENTS PRESENT:    Y    N

SIGNATURES:
    SURGICAL TECH: _____
    NURSE: _____

I/WE HAVE REVIEWED THE PERTINENT CLINICAL RECORDS, INCLUDING RADIOGRAPHS, AND CONFIRMED THE ABOVE TO THE CORRECT.

SURGEON SIGNATURE: _____

PEEL

Fig. 8 — 16

SURGICAL PEN/LABEL A                                    PEEL

Fig. 9 — 42

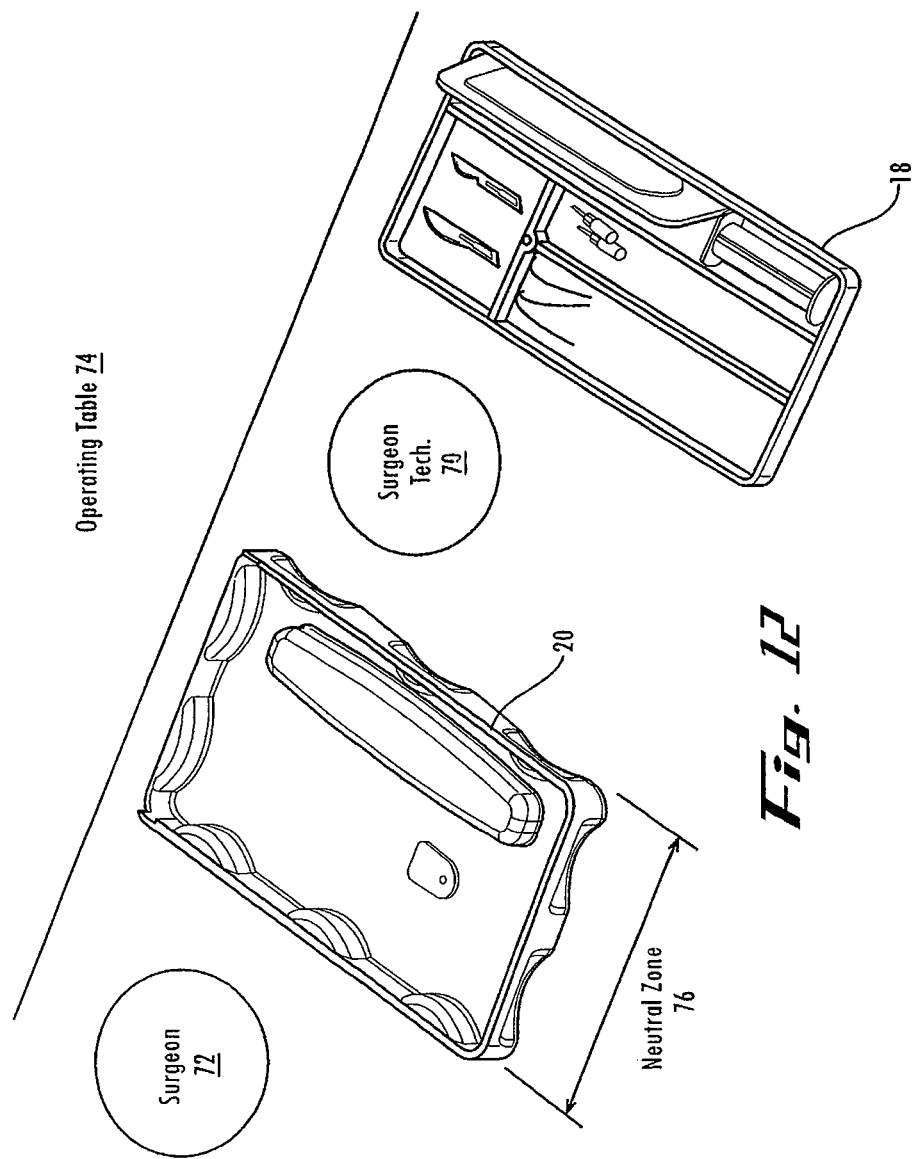

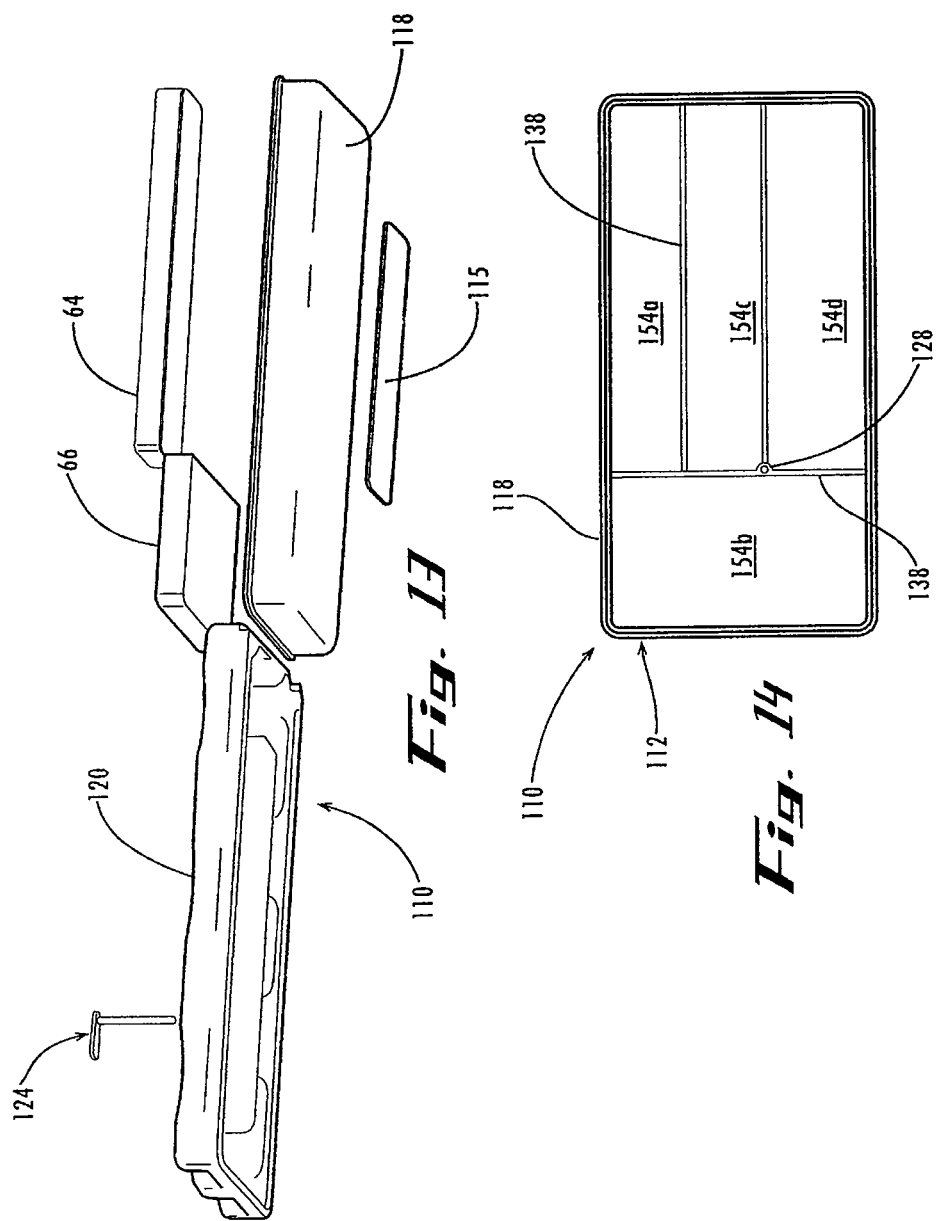

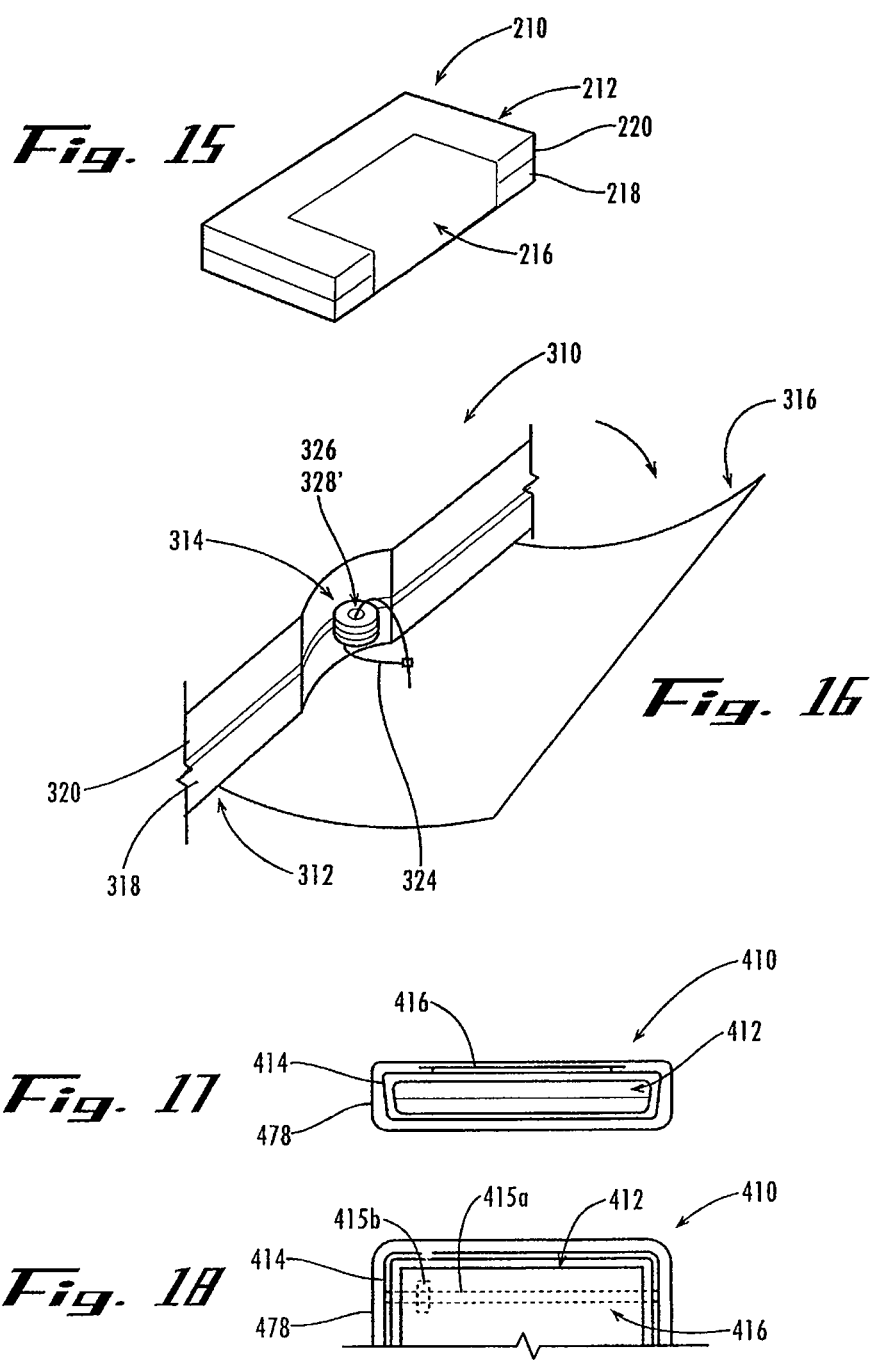

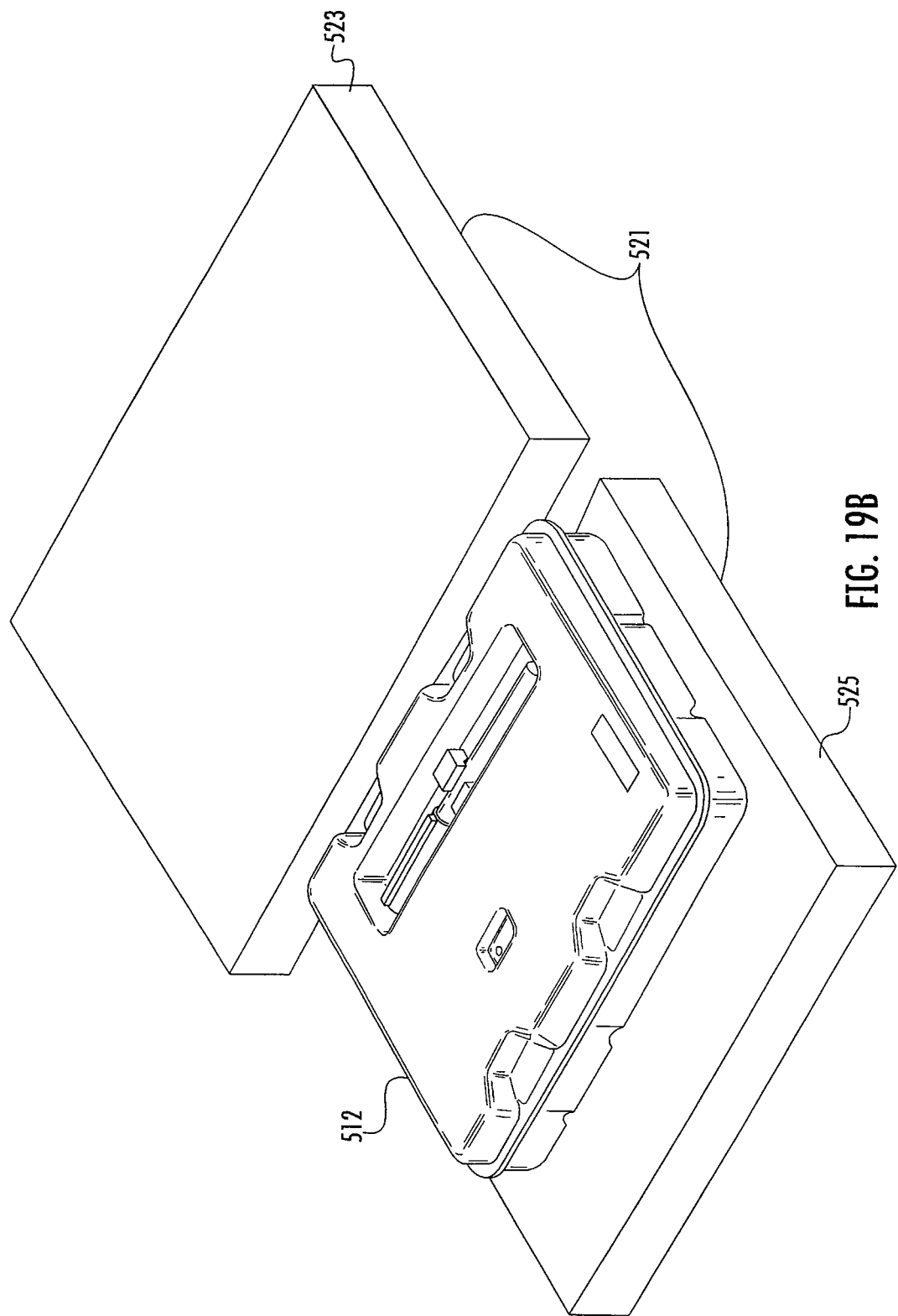

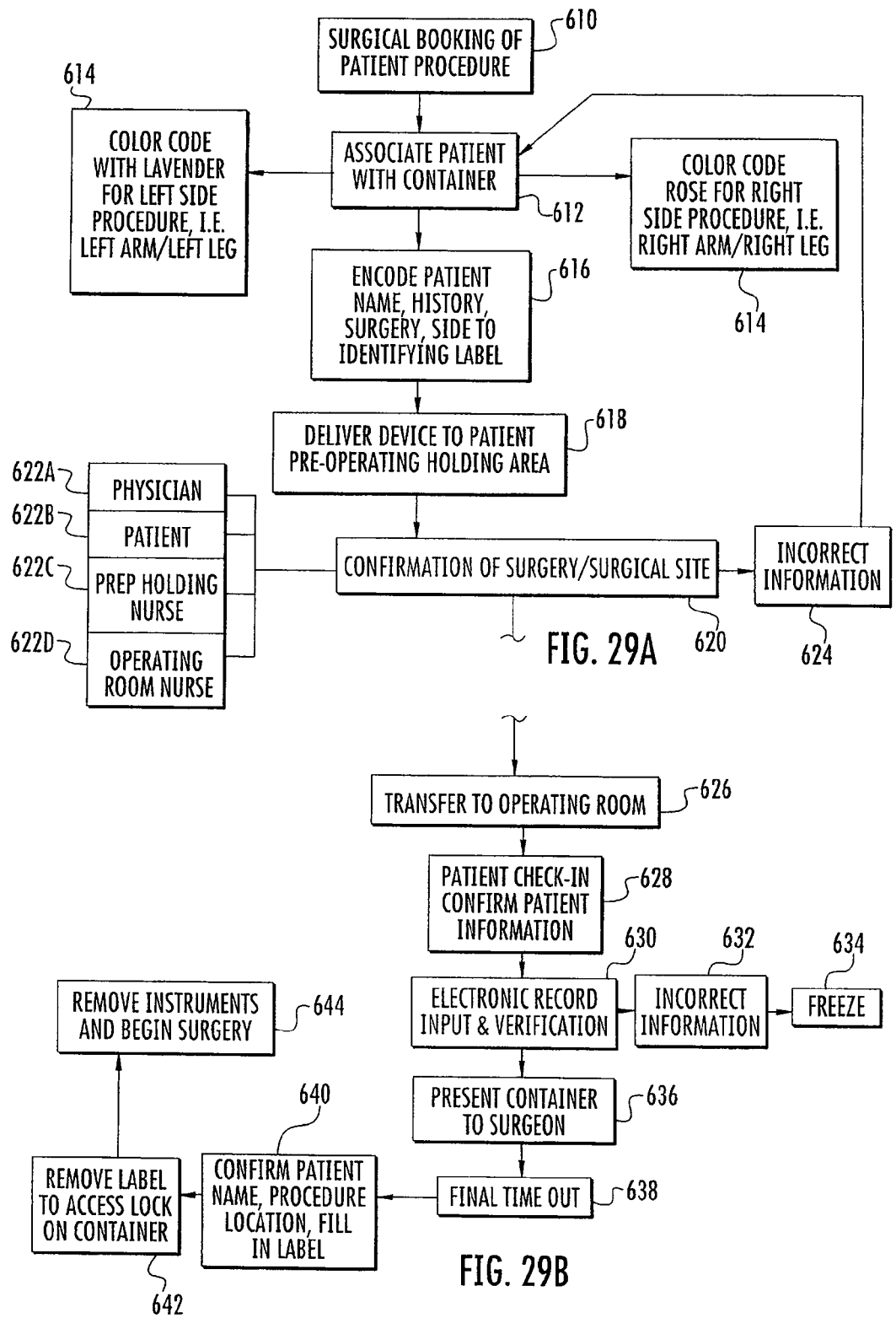

SYSTEM AND METHOD FOR PREVENTING WRONG-SITE SURGERIES

CROSS-REFERENCE TO RELATED APPLICATION

In accordance with 37 C.F.R 1.76, a claim of priority is included in an Application Data Sheet filed concurrently herewith. Accordingly, the present invention claims priority as a continuation-in-part of U.S. patent application Ser. No. 14/143,920, entitled "SYSTEM AND METHOD FOR PREVENTING WRONG-SITE SURGERIES" filed Dec. 30, 2013, now U.S. Pat. No. 9,168,107, which is a continuation-in-part of U.S. patent application Ser. No. 11/270,686 entitled "SYSTEM AND METHOD FOR PREVENTING WRONG-SITE SURGERIES", filed Nov. 9, 2005, now U.S. Pat. No. 8,616,215 issued Dec. 31, 2013, which claims priority to U.S. Provisional Patent Application No. 60/626,240, filed Nov. 9, 2004, entitled "SURGERY START BOX". The contents of each of the above referenced applications are herein incorporated by reference in its entirety.

TECHNICAL FIELD

The present invention relates generally to surgical devices and procedures and, in particular, to surgical devices and procedures for preventing wrong-site surgeries.

BACKGROUND OF THE INVENTION

A great deal of attention has recently been given to the unacceptable rate of avoidable patient injuries, or so-called medical mistakes, in the United States. Estimates of the number of medical mistakes per year in the United States is difficult to ascertain, but a recent publication, *To Err is Human*, by Dr. Lucian Leape, suggests that the avoidable death rate for medical mistakes are between 48,000 and 96,000 patients per year.

As defined by the Joint Commission on Accreditation of Healthcare Organizations (JCAHO), wrong-site surgery includes wrong side or site of the body, wrong procedure, and wrong-patient surgeries.

Prevalence of Wrong-Site Surgery

From January 1995 to March 2001, JCAHO reviewed voluntary reports of 1,152 "sentinel events." Wrong-site surgery accounted for 114 cases (9.9%) and included procedures in neurosurgery, urology, orthopedics, and vascular surgery. Despite the high profile of JCAHO's Sentinel Event Policy, under-reporting by healthcare organizations likely affects these statistics. Only 66% of the 1,152 total events were "self-reported" by the institutions involved; the balance coming from patient complaints or media stories. Using a mandatory reporting system, the New York State Department of Health received 46 reports of wrong-site surgery from Apr. 1, 1998 through Mar. 31, 2000, compared with 114 cases JCAHO received nationally over a period 3 times longer. This suggests that voluntary incident reporting may grossly underestimate the true incidence of wrong-site surgery by a factor of 20 or more.

The Physician's Insurance Association of America (PIAA) reviewed the claims data from 22 malpractice carriers representing 110,000 physicians from 1985 to 1995. There were 331 cases of wrong-site surgery. The complete PIAA database documents almost 1,000 closed malpractice claims involving wrong-site surgery. However, this figure also likely underestimates the prevalence of wrong-site surgery. Since most wrong-site surgeries involve relatively minor procedures (arthroscopy, rather than limb amputations or major neurosurgical procedures), sequelae are minimal and may not result in a claim. Consequently, estimates of the incidence of wrong-site surgery derived from litigation data likely underestimate the true prevalence of this problem, as do estimates based on incident reports.

Factors Identified as Contributing to Wrong-Site Surgery

Several factors have been identified that may contribute to an increased risk of wrong-site surgery. These risk factors include:

More than one surgeon involved in the case, either because multiple procedures were contemplated or because the care of the patient was transferred to another surgeon;

Multiple procedures were conducted on the same patient during a single trip to the operating room, especially when the procedures were on different sides of the patient;

Unusual time pressures related to an unusual start time or pressure to speed up the preoperative procedures; and Unusual patient characteristics such as physical deformity or massive obesity that might alter the usual process for equipment set-up or positioning of the patient.

The root causes identified by hospitals were most often related to communication, preoperative assessment of the patient, and the procedures used to verify the operative site.

Communication issues fall into two major categories:

Failure to engage the patient (or family, when appropriate) in the process of identifying the correct surgical site, either during the informed consent process or by the physical act of marking the intended surgical site; and Incomplete or inaccurate communication among members of the surgical team, often through exclusion of certain members of the team (e.g., surgical technicians) from participation in the site verification process, or through reliance solely on the surgeon for determining the correct operative site.

The completeness of the preoperative assessment of the patient was a frequent contributing factor, often through failure to review the medical record or imaging studies in the immediate preoperative period. The procedures for verifying the correct operative site were found to be flawed in many cases due to:

No formal procedure;

No final check in the operating room;

The absence of any oral communication in the verification procedure;

All relevant information sources not available in the operating room;

No checklist to ensure all relevant information sources were checked;

Some members of the surgical team were excluded from the verification process and felt they were not permitted to point out a possible error; and Total reliance on the surgeon for verifying the surgical site.

JCAHO Strategies for Reducing Wrong-Site Surgery

The Joint Commission offers the following possible strategies for reducing the risk of wrong-site surgery:

Clearly mark the operative site and involve the patient in the marking process to enhance the reliability of the process;

Require an oral verification of the correct site in the operating room by each member of the surgical team;

Develop a verification checklist that includes all documents referencing the intended operative procedure and site, including the medical record, X-rays and other imaging studies and their direct observation of the marked operative site on the patient;

Personal involvement of the surgeon in obtaining informed consent;

Ensure through ongoing monitoring that verification procedures are followed for high-risk procedures; and "Time out" immediately before starting the procedure. (Source: Joint Commission on Accreditation of Healthcare Organizations. Sentinel Event Alert, issue six, Aug. 28, 1998.)

Despite the implementation of strategies to prevent wrong patient, wrong site, wrong side surgery, regrettably this seemingly most preventable of complications still occurs. (The aforementioned statistics do not address the number of times in which implants or instrumentation is going to be placed as a part of the procedure, and are not available when the surgeon is ready for them. In these instances, the surgeon must either change plans, or wait while the surgical team attempts to locate the appropriate implants or instrumentation, which, in some instances, is located at another hospital.) The incorrect assumption of a medical professional's infallibility, coupled with organized medicine's focus on the individual's medical mistakes rather than a systems approach have contributed to this problem. In an attempt to improve patient safety, "[e]ffective Jul. 1, 2004, compliance with the *Universal Protocol for Preventing Wrong Site, Wrong Procedure, Wrong Person Surgery* will be required of all Joint Commission accredited organizations." As a part of the universal protocol, a "pause" or "time out" is required. This serves as a final verification of: (1) the correct patient; (2) the correct procedure, site and side; and as applicable, (3) the availability of implants or instrumentation, prior to making incision. This is a time when all members of the surgical team are supposed to pause to review the case, and agree that the correct procedure is being done on the correct patient, at the correct site, and on the correct side. In theory, this would ensure that any errors that had been made could be detected prior to incision. In reality, the "time out" seldom occurs; and when it does, not in any uniform or regular manner. Without a uniform or regular procedure, ritualized compliance, i.e. going through the motions results in many institutions. The universal protocol cannot enforce a pause and does not specify a protocol as to what should happen during a pause. The universal protocol does not specify a particular time for the pause to occur, and it does not specify a protocol as to what should happen during the pause, that is to say, what information should be communicated by whom, and to whom. While guidelines may be suggested, each institution determines how to comply, therefore standardization is not achieved.

Accordingly, it can be seen that a need exists for improvements to surgical procedures and devices to prevent or at least reduce wrong-site surgeries. It is to the provision of meeting these and other needs that the present invention is primarily directed.

SUMMARY OF THE INVENTION

Generally described, the present invention provides a system and method for preventing wrong-site surgeries by imposing a pause just before the surgery starts, during which time the surgical team conducts a pre-operative assessment to confirm that correct site of the surgery about to be performed. By imposing the pre-operative assessment, the surgical team gets one last chance to catch any avoidable mistake that would otherwise lead to a wrong-site surgery.

In a first example embodiment of the present invention, the system includes a container that holds one or more surgical implements, a lock mechanism for securing the container closed, and a removable confirmation label that blocks or at least impedes access to the lock mechanism. The surgeon cannot readily open the container to get the surgical implements until the correct surgical site has been confirmed and the label has been removed. The surgical implements include one or more scalpels or other blades, a syringe loaded with a local anesthetic, a needle, a scope, and/or other surgical implements needed at the outset of the surgery. The label includes, for example, a checklist for confirming surgery-related information and one or more fields for signatures.

In one aspect of the invention, the lock mechanism includes a lock member that fits through two openings in the container that align when the container is closed. Preferably, the container includes a bottom and a top that slides off the bottom, with one lock opening being through the top, and the other lock opening formed into an internal divider wall that also defines compartments for the surgical implements.

In another aspect of the invention, the container bottom has one or more dedicated compartments for surgical needles. In use, the bottom may be positioned beside a surgical team member for storing surgical needles after they have been used in the surgery. Then, at the conclusion of the surgery, the container may be closed and the surgical sharps all safely disposed of at once.

In yet another aspect of the invention, the container top can be removed from the bottom and positioned between the surgeon and a surgical team member to define a neutral zone where hands do not meet. With the neutral zone clearly defined, the incidence of stickings when passing the surgical sharps back and forth is reduced.

In another aspect of the invention, the container can be adapted to be tracked and/or monitored using, for example, a data capture and/or display device, system or technology secured to at least one portion of said container.

In another aspect of the invention, the container can be adapted to provide a quick and easy visualization mechanism to relate to the surgical team the correct site, i.e. left side or right side, the surgical procedure should occur.

In another aspect of the invention, systems and methods which utilize a physical device to implement and enforce a universal standard are provided. Applicant's methods and systems are the first to track a series of data points which can be analyzed to provide wrong site surgery near miss data and wrong site surgery error data. Such tracking and data collection enables an institution to improve their processes handling wrong site surgeries with objective data, relevant to their own institution.

In another aspect of the invention, a system and method of consistently producing, capturing, and storing reliable and data mineable wrong site surgery data is provided. The systems and methods include electronic wrong site surgery near miss data or electronic wrong site surgery error data, or an electronic patient surgical profile. The systems and methods may be utilized to support organizational and governmental process improvement initiatives to greatly reduce and prevent wrong-site surgeries across hospital systems.

In use, the system forces a surgery team to pause prior to initiating the surgery, after the patient is draped and the surgeon and surgical technician are both sterilely gowned, when all members of the surgical team pause to make sure that they have the correct patient, the correct operation is being performed, on the correct site and side, and all necessary surgical instrumentation or implants are physically available. Once that information is confirmed, which might require the surgeon to review the medical record or the imaging studies; the surgeon removes a dual-tipped pen from the top of the container and uses the ink side to sign the label on the box. The label is then removed and placed in the medical record, and the surgeon now has access to the lock to open the container and remove the surgical implement(s). The surgical marking pen side of the pen can be used to mark the incision. The container top is then turned upside down and serves as the surgical neutral zone, which defines a hands-free "neutral zone" where sharp instruments can be traded between the surgeon and surgical technician without the actual passing of sharp instruments from hand to hand. In addition, the container may also have pre-loaded local anesthetic with a needle and syringe, to further expedite the starting of the operation. Furthermore, compartments in the container will have foam padded areas, with printed numbers, for the counting and storage of suture needles, as well as other sharps, and at the end of the surgical case the container can be reclosed securely, with all the sharps in the container accounted for, and safely disposed of as one unit.

In a second example embodiment, the container bottom has four compartments with a shorter syringe compartment. In a third example embodiment, the label is attached to the top and bottom of the container to lock it closed, so that the label doubles as the lock. In a fourth example embodiment, the lock member is provided by a tie member that fits through aligned openings formed by two external tabs on the container, and the label covers the lock member. In a fifth example embodiment, the lock member is provided by a wrapper that encloses the container, and the label is removably attached to the wrapper or to a pull tab for opening the wrapper. And, in still other embodiments, the container does not include a lock mechanism, or it does include a lock mechanism and the label does not cover it, but the label impedes access to opening the container by being prominently positioned so that it is hard not to notice it, which prompts a pause for the surgical team to conduct the pre-operative assessment to confirm the correct site of the surgery.

The method of preventing wrong-site surgery comprises the steps of providing a container that holds a surgical implement and has a label for confirming surgery-related information, with the label removably attached to the container; using the label to conduct a pre-operative assessment confirming a correct surgical site; removing the label from the container; opening the container and removing the surgical implement; and using the surgical implement at the outset of the surgery. In this way, the pre-operative assessment confirming that the correct surgical site has been identified is done before making an incision and starting the surgery. Preferably, the container is provided with a lock mechanism securing it closed, and the label is positioned blocking access to the lock mechanism so that the label must be removed to open the container.

In one aspect of the method, the container includes a top that is removed to open the container. The method further includes the steps of positioning the removed container top between a surgeon and a surgical team member to define a neutral zone where hands do not meet; and exchanging surgical sharps between the surgeon and the surgical team member without sticking each other. The exchanging is done by the surgeon placing the surgical sharps into the container top and the surgical team member then picking them up, and vice versa.

In another aspect of the method, the container includes a bottom with at least one compartment that holds the surgical implement and with one or more additional compartments for surgical needles, and positioning the removed container bottom beside a surgical team member. The method further includes the steps of, after the surgical needles have been used in the surgery, storing the used surgical needles in the dedicated compartments in the container bottom. In addition, the method includes replacing the top on the container to close the container at the conclusion of the surgery; and disposing of the container with the used sharps safely inside.

The specific techniques and structures employed by the invention to improve over the drawbacks of the prior devices and accomplish the advantages described herein will become apparent from the following detailed description of the example embodiments of the invention and the appended drawings and claims.

BRIEF DESCRIPTION OF THE DRAWINGS

FIG. 4 is a perspective view of the container of FIG. 1 in an unlocked and open position;

FIG. 5 is a cross section view of the container of FIG. 1 taken at line 5-5, showing a lock member being removed from aligned lock openings to unlock the container;

FIG. 6 is a perspective view of the lock member of FIG. 5;

FIG. 7 is a plan view of an instructions label of FIG. 3;

FIG. 8 is a plan view of the confirmation/signature label of FIG. 3;

FIG. 9 is a plan view of a surgical pen-covering label of FIG. 3;

FIG. 12 is a schematic diagram of the container shown in FIG. 10 in use, showing the container bottom holding the surgical sharps and the container top inverted and defining a neutral zone between the surgeon and the surgical technician;

FIG. 13 is an exploded perspective view of a container for surgical sharps according to a second example embodiment;

FIG. 14 is a plan view of the bottom of the container of FIG. 13;

FIG. 15 is a perspective view of a container for surgical sharps according to a third example embodiment, showing the container in a closed and locked position;

FIG. 16 is a perspective detail view of a container for surgical sharps according to a fourth example embodiment, showing a label being removed to expose a lock;

FIG. 17 is a side view of a container for surgical sharps according to a fifth example embodiment, showing a label positioned on a sterile inner wrapping enclosed by an outer wrapping;

FIG. 18 is a plan detail view of the container of FIG. 17, showing an opener strip and pull tab of the sterile inner wrapper;

FIG. 19B is a perspective view of an alternative embodiment of the container for surgical equipment, illustrating an outer container.

FIGS. 29A and 29B illustrate a flow chart describing an representative embodiment of a method of preventing a wrong-site error during surgery in accordance with the present invention;

DETAILED DESCRIPTION OF EXAMPLE EMBODIMENTS

Figure 1:
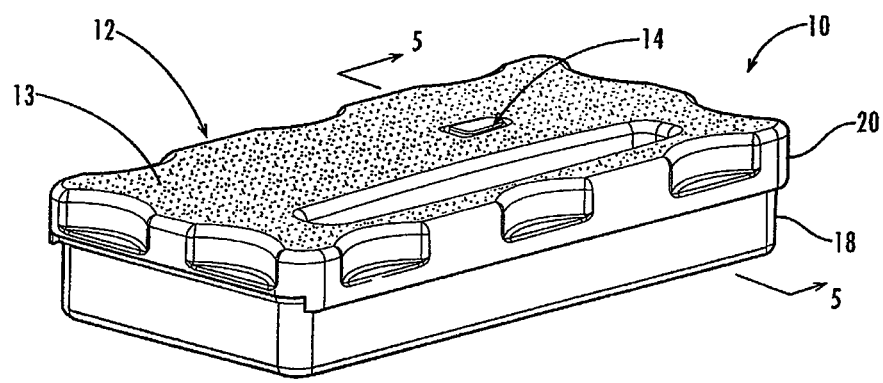
FIG. 1 is a perspective view of a container for surgical sharps according to a first example embodiment of the invention, showing the container in a closed and locked position.
Figure 2:
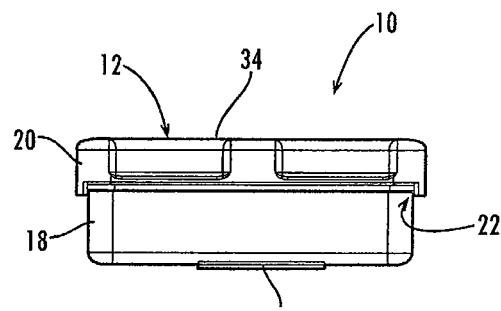
FIG. 2 is a left side view of the container of FIG. 1.
Figure 3:
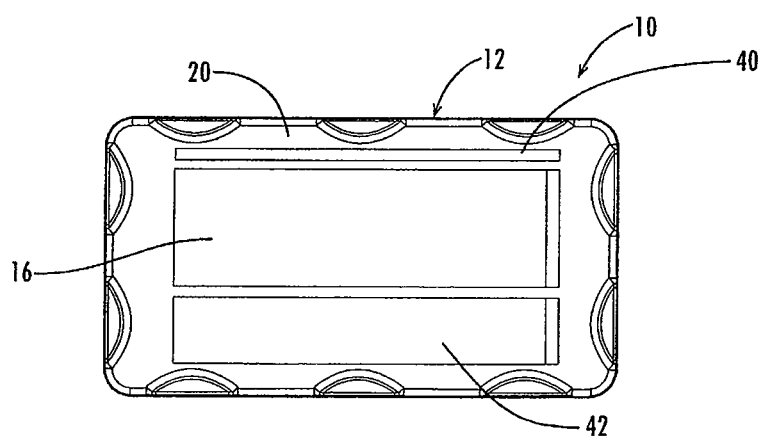
FIG. 3 is a plan view of the container of FIG. 1, showing labels on the container, including a confirmation/signature label covering a lock member so that the container cannot be unlocked and opened until the label is removed.

Referring to the drawing figures, the present invention includes a surgical system and a method of using the surgical system to impose a pre-operative assessment to prevent wrong-site surgeries. The system includes a container that holds one or more surgical implements needed for the surgery, a lock mechanism that secures the container in a closed position, and a confirmation and/or signature label in a position that prevents or at least impedes access to the lock. In this way, the surgical team is forced to pause to deal with the label in order to access the surgical implements needed to start the surgery.

Referring to FIGS. 1-11, where is illustrated a surgical system 10 according to a first example embodiment of the present invention. FIGS. 1-4 show the surgical container 12, the lock mechanism 14, and the confirmation and signature label 16 of the surgical system 10. The container 12 has a bottom 18 and a top 20 that can be positioned in the closed position of FIG. 1 or the opened position of FIG. 4. In the depicted embodiment, the top 20 and the bottom 18 slide relative to each other to open and close the container 12. For example, the container 12 may include a lip-and-groove arrangement 22 to permit the top 20 to be slid off of the bottom 18. In addition, the container 12 may include detents or other structures for snapping closed the top 20 and bottom 18 so that the container cannot freely slide open when it is unlocked. In alternative embodiments, the container has a hinge for a pivotal opening motion, preferably with the hinge permitting the top to be separated from the bottom. The size of the container 12 is selected based primarily on the intended contents and may be customized for different types of surgeries and/or different surgeons. In general, though, the container 12 is not too large to be obtrusive or too small to escape notice. In a typical commercial embodiment, the container 12 is about 1-2 inches high, about 4-6 inches wide, and about 8-10 inches long. In addition, the container 12 is preferably generally rectangular with scalloped top edges for ease of gripping, and is preferably made of a plastic material, though other materials may be suitably employed.

Preferably, the bottom surface of the bottom 18 and the top surface of the top 20 are provided with gripping features so that they will not slip on a substantially horizontal surface they are resting upon. For example, the gripping features may include a layer 13 of frictional material such as rubber or soft plastic inlayed or applied onto the top surface (or a portion thereof) of the top 20, and an adhesive-backed pad 15 of frictional material such as rubber or soft plastic attached to the bottom surface of the bottom 18. In this way, the bottom 18 and the inverted top 20 are held in place during use, as described in detail below.

Referring additionally to FIGS. 5 and 6, the lock mechanism 14 secures the container 12 in the closed position. The lock mechanism 14 preferably includes a lock member that is received in locking engagement through two aligned lock openings in the top and bottom of the container. For example, in the depicted embodiment the lock member 24 linearly slides into a first lock opening 26 in the top 20 and a second lock opening 28 in the bottom 18 when the container 12 is in the closed position. The lock member 24 preferably includes a lock pin 32 that is received in the aligned openings 26 and 28 and a tab 34 for ease of grasping by hand. The top 20 may have a recess 36 configured to at least partially receive the tab 34 to provide a low profile, with the first lock opening 26 positioned within the recess. The second lock opening 28 is preferably formed into one or more divider walls 38 that define compartments in the bottom 18, so that the opening is out of the way and so a separate upstanding structure is not required for defining the opening. The lock member 24 can be made of a plastic, metal, or other material. It will be understood that other types of lock mechanisms may be used to accomplish the herein-described purposes.

Referring additionally to FIGS. 7-9, the confirmation and signature label 16 is removable and covers the lock member 24 so it cannot be accessed to unlock the container 12 until the label is removed. In a typical commercial embodiment shown in FIG. 8, the confirmation and signature label 16 has a front side that can be written upon and that includes a checklist to be filled out by the surgical technician, and fields where surgical team members sign after confirming that the information entered in the checklist is correct. For example, the checklist preferably provides for confirming the correctness of the patient name, the type/name of the surgical procedure, the laterality of the incision (left, right, or midline), and the laterality of the pathology (left, right, or midline), and for confirming that the proper instrumentation and any surgical implants are present and accounted for. It will be understood that the confirmation and signature label 16 may be customized for the same or other surgical uses, and thus is not limited to the specific representation depicted herein. Thus, in alternative embodiments, the checklist may call for the same surgery-related information of the depicted embodiment, only some of this information, or additional information. Preferably, the confirmation and signature label 16 is adhesive-backed and has a pull tab so that it can be easily removed from the container 12 and, if desired, placed in the medical record (the patient's record/chart/file) after it has been signed and removed.

In addition, the container 12 preferably has instructions for use prominently displayed on it. For example, in the depicted embodiment the instructions are marked on an adhesive-backed label 40 that is applied to the container top 20. Alternatively, the instructions may be printed or otherwise marked directly on the container 12 or elsewhere, or they may be omitted.

Figure 10:
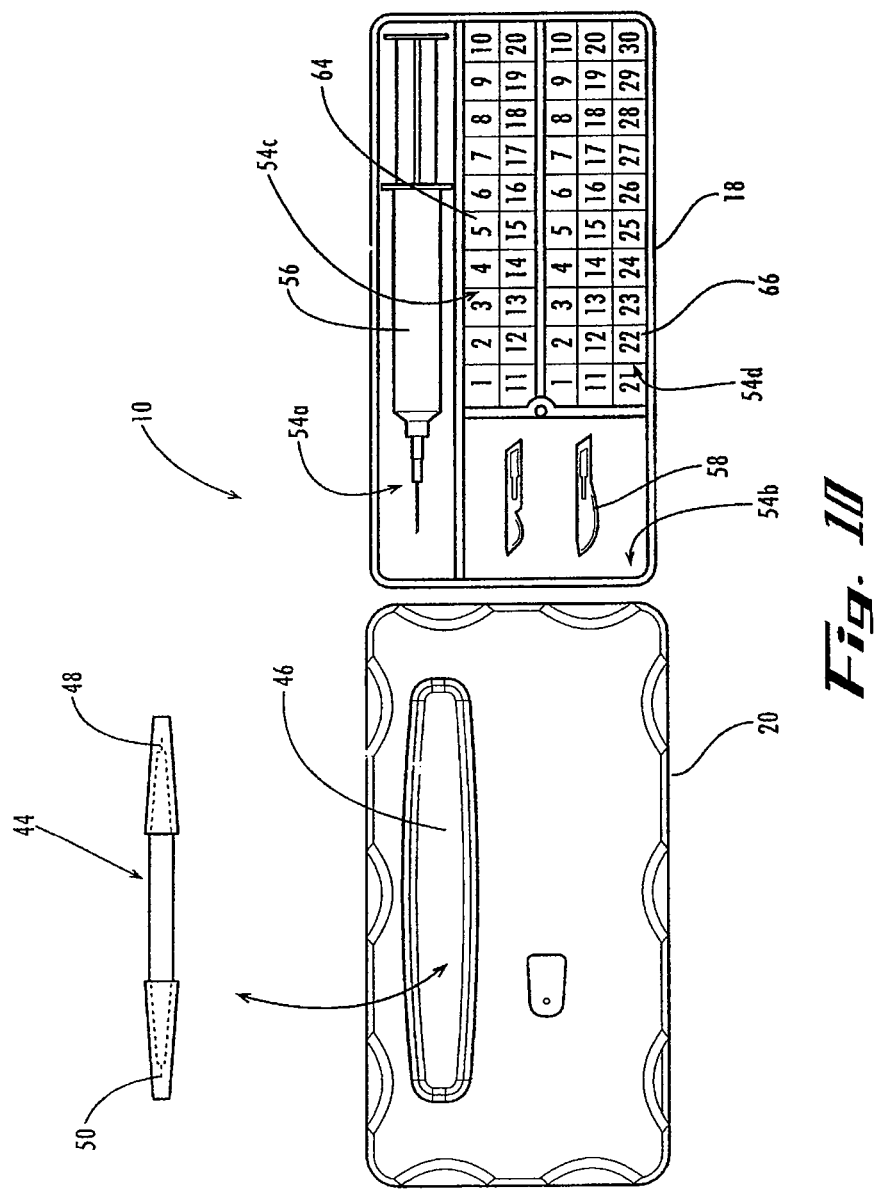
FIG. 10 is a plan view of the container of FIG. 1, ready for use, showing compartments holding a local anesthetic-loaded syringe and surgical blades for use in the surgery, and empty compartments for used suture and syringe needles.

Referring additionally to FIG. 10, the container 12 preferably has an adhesive-backed label 42 applied to the container top 20 to cover and hold a pen 44 within a recess 46 formed in the container top 20. The pen 44 preferably has two marking tips 48 and 50 at opposing ends. A writing tip 48 is similar to a conventional ink pen for filling in and signing the confirmation and signature label 16. And a surgical tip 50 is similar to a conventional surgical pen with indelible ink for pre-operatively marking the surgical site on the patient's body, and optionally for the signature of the surgeon. In alternative embodiments, the pen 44 may be removably attached to the container 12 by hook-and-loop fasteners or other conventional attachment structures; the pen 44 may be a conventional one-tipped ink or surgical pen, or it may be omitted. In addition, a small measuring ruler may be included in the recess 46 or provided (e.g., etched, printed, or otherwise applied) on the container, for example, at location 52 (FIG. 4).

The bottom 18 of the container 12 preferably includes a number of internal compartments (collectively referred to as the compartments 54) defined by the internal divider walls 38. The size, shape, and configuration of the compartments 54 are selected for the surgical implements desired to be held in the container 12, and as such may be customized depending on the surgery and the surgeon. In the depicted embodiment, the container 12 has a first compartment 54a that is pre-loaded with a syringe 56 containing a local anesthetic such as lidocaine, and a second compartment 54b that is pre-loaded with one or more surgical blades 58, such as Number 10 and 15 scalpels. It will be understood that the container 12 may be provided with both the syringe 56 and the blades 58, with only one of these, and/or with other surgical implements such as packets of surgical needles. In alternative embodiments, the compartments are sized, shaped, and configured for including other types of blades, handles for the blades, disposable single-unit scalpels, a syringe with another local anesthetic, arthroscopic probes, and/or other surgical implements needed to start the case. In addition, the second compartment 54b for the blades 58 may have a sheet of foam lining.

Figure 11:
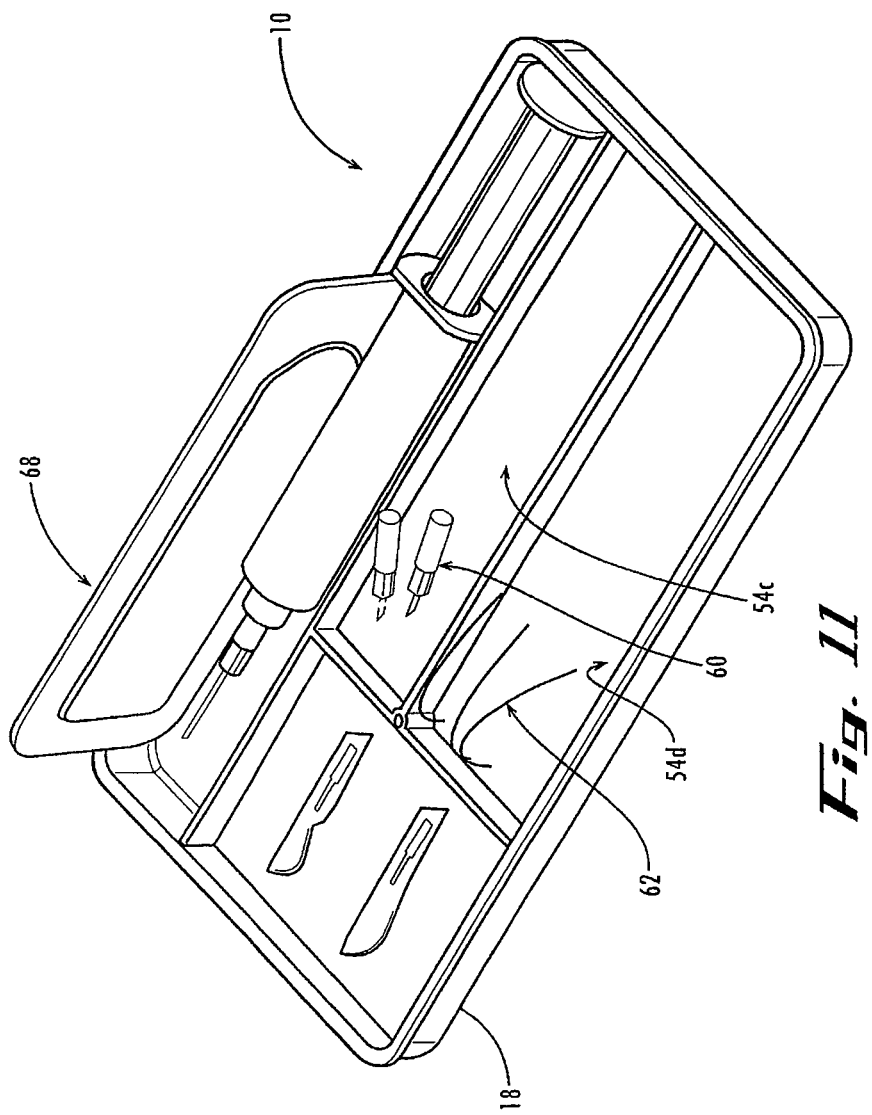
FIG. 11 is a perspective view of the container bottom of FIG. 10 in use, showing the used surgical suture and syringe needles stored in their dedicated compartments.
Figure 19A:
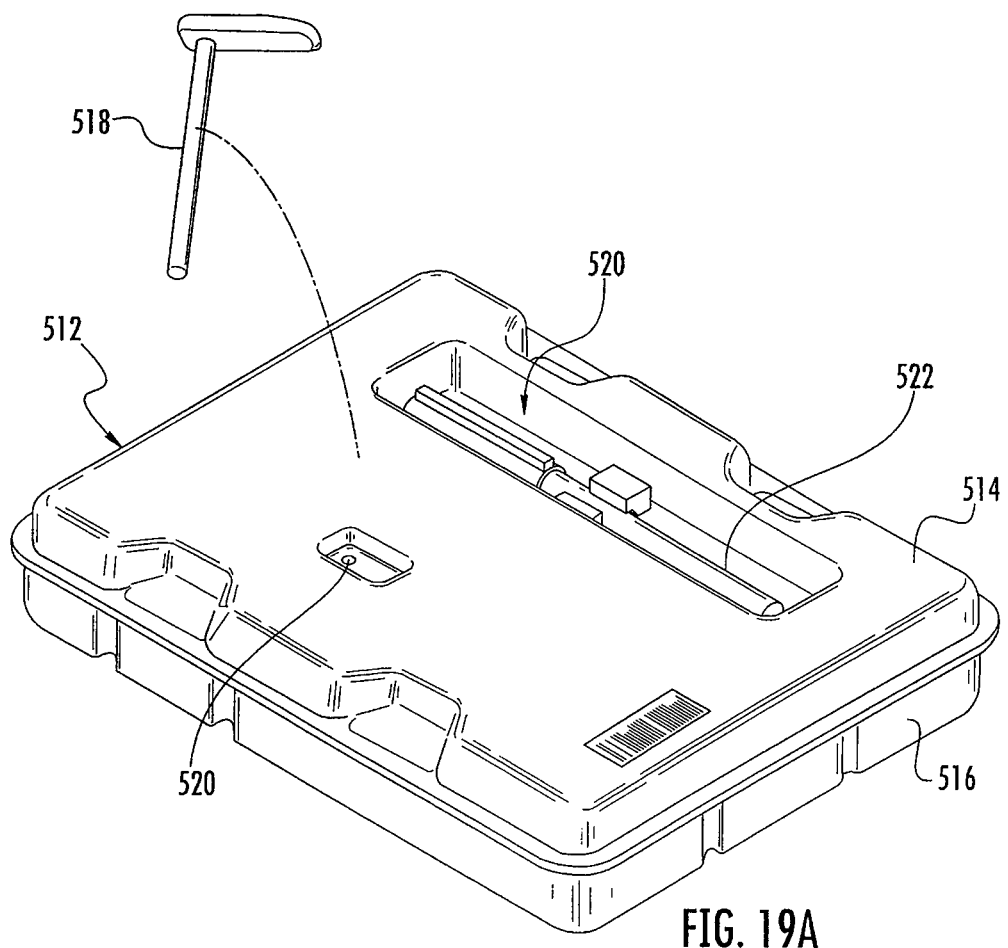
FIG. 19A is a perspective view of a container for surgical equipment according to an alternative embodiment of the invention, showing the container in a closed position.
Figure 20:
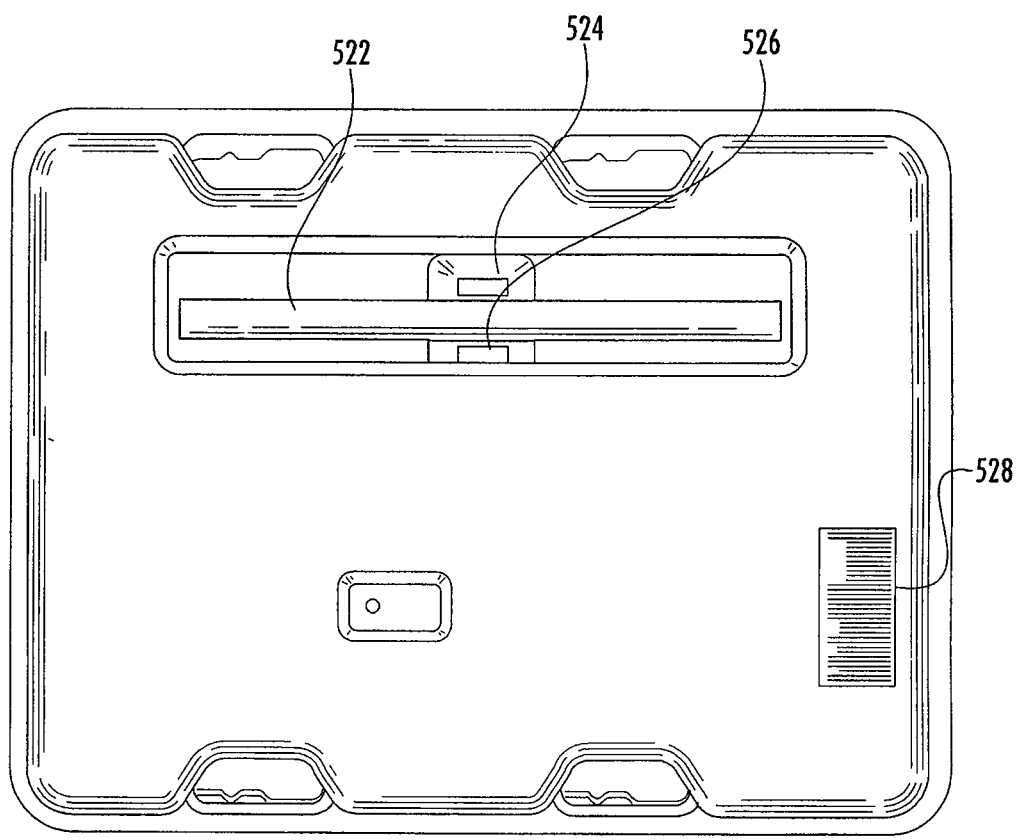
FIG. 20 is a top view of the container of FIG. 19.

Referring additionally to FIG. 11, the depicted container 12 has a third compartment 54c and a fourth compartment 54d that are sized, shaped, and configured for storing used syringe and suture needles 60 and 62 after they have been used in the surgery. The compartments 54c and 54d are preferably each lined with an attachment sheet 64 and 66 that holds the used needles in place and that has numbered spaces for ease in counting the used needles. For example, the attachment sheet 64 and 66 may be made of a foam and/or magnetic material. In addition, the first compartment 54a can be used for miscellaneous purposes such as holding unused suture packages 68 so they are readily accessible as needed during the surgery. Thus, it will be noted that the container bottom 18 of FIG. 10 is shown just opened and ready for use, and the container bottom 18 of FIG. 11 is shown in the midst of use during the surgery.

A method of using the system 10 to prevent wrong-site surgeries will now be described. The container 12 is provided in the closed, locked position of FIGS. 1-3, preloaded with one or more surgical implements needed to start the surgery. The confirmation and signature label 16 prevents accessing the lock member 24, so the surgical team must deal with the label before it can unlock and open the container 12 to start the surgery. This effectively forces a pause or "time out" before the surgery can commence, thereby prompting the pre-operative assessment. At this time, the surgical technician who is starting the case fills out the checklist on the label 16. For example, when using the confirmation and signature label 16 of FIG. 8, the surgical technician checks for the correct patient being present, the correct type/name of the surgical procedure, the correct laterality of the incision (left, right, or midline), the correct laterality of the pathology (left, right, or midline), and the presence of the proper instrumentation and/or needed surgical implants. The attending surgeon then confirms all the information written on the confirmation and signature label 16 by the surgical technician and signs his name to indicate that he/she has personally reviewed and confirmed the information to be correct. Then the surgeon (or the technician) removes the confirmation and signature label 16 from the container 12, removes the lock member 24 (or otherwise actuates the lock mechanism to unlock the container), and opens the container 12 (see FIG. 4) to access the surgical implements in the container. The removed confirmation and signature label 16 can be placed in the medical record to document that the "time out" and confirmation was performed. At this point, the surgery start time is recorded, and surgery is considered started.

The individual hospital's operating room policy preferably requires the operating/attending surgeon to open the box him/herself, and/or to sign his/her name prior to making incision. In this way, the system 10 forces the surgical team to pause at the same time in every case (namely, just prior to incision), to ensure that the correct surgery is being done, on the correct side, to the correct patient, and that all needed surgical instrumentation or implants are available. It will be understood that other surgical systems that include a container for surgical implements and a confirmation and/or signature label that is positioned to block or impede opening of the container to force a pause just before the start of a surgery, but not specifically described herein, may be used with the system to accomplish the functionality described herein. It should also be noted that the system 10 is not meant to replace current pre-operative measures to prevent wrong-site surgery (I.e., all of JHACO's advice/recommendations), though it could, but rather it is designed to supplement those measures by providing a last chance to prevent wrong-site surgery by forcing the pause just before the incision.

The uniqueness of the system 10 provides additional safety features. One of these safety features relates to the "neutral zone," which is generally considered to be the area between the surgeon and the surgical technician, where the surgeon's hands and the surgical technician's hands are supposed to never meet. But in practice, this is a general and undefined area, and it can expand, shrink, and shift as the surgeon and technician lean over, turn slightly to one side, and/or shift their weight during the course of the surgery. Because of this, and because of the focus on the patient and the surgical procedure, occasionally the surgeon and technician stick each other when passing sharp instruments back and forth.

Referring additionally to FIG. 12, after the container 12 has been opened to start the surgery, the container top 20 may be inverted and placed on a cart or other horizontal surface between the surgical technician 70 and the surgeon 72 as they face the operating table 74. As described above, the top surface of the container top 20 and the bottom surface of the container bottom 18 preferably have gripping features so that they do not slip and move during the surgery. In this position, the container top 20 defines a clearly demarcated, lateral neutral zone 76 where hands are not allowed to meet. When the surgeon 72 is done with a sharp instrument, he can simply place it in the neutral zone, that is, in the upside-down container top 20. The surgical technician 70 can likewise add or remove sharp instruments to or from the inverted container top. By the surgeon 72 and the surgical technician 70 never actually handing each other sharp instruments, but instead having a clearly defined neutral zone 76 for indirectly passing sharps to each other, the incidence of needle sticks can be reduced.

Furthermore, the container bottom 18 may be placed on a cart or other horizontal surface beside the surgical technician 70 (e.g., on the opposite side of the container top 20) or elsewhere in a position that is convenient for the technician. With the container bottom 18 accessible to the technician 70, he/she can use the container bottom during the surgical case to store all the used sharps (e.g., scalpels, needles), as shown in FIG. 11, similarly to how the technician would normally use a conventional sharps box or needle holder or counter. The container 12 or at least its top 20 may be red in color, similar to a conventional sharps box, to help minimize the likelihood of needle sticks. Alternatively, another color such as purple or opaque may be used.

Moreover, at the end of the case, all the sharps used during the surgery can be put in the container 12, and the container can be closed and safely disposed of. The detents or other snapping structures of the container 12 hold the container closed. In addition, the lock mechanism 14 may be provided with detents or other snapping structures so that the lock member can be reinserted to secure the container 12 closed. This way, all of the surgical sharps used during the case can be safely disposed of as a single unit.

Turning now to FIGS. 13 and 14, there is illustrated a surgical system 110 according to a second example embodiment of the present invention. Similarly to the system 10 of the first example embodiment, the system 110 includes a container 112 with a bottom 118 and a top 120, a lock mechanism having a lock member 124 that is received in alignable first opening 126 (not shown) and second opening 128, and a number of divider walls 138 forming compartments 154 for the surgical implements. In this embodiment, however, compartment 154b extends all the way across the container bottom 118, and compartments 154a, 154c, and 154d each have the same length. In addition, the foam sheet inserts 64 and 66 for the compartments are configured for the different arrangement of the compartments.

Turning now to FIG. 15, there is illustrated a surgical system 210 according to a third example embodiment of the present invention. The system 210 is similar to that of the above-described embodiments, having a container 212 with a bottom 218 and a top 220 and a confirmation and signature label 216. In this embodiment, however, the label 216 is positioned extending across the bottom 218 and top 220 of the container 212 to hold it closed. In this way, the label 216 also functions as the lock mechanism, so a separate lock mechanism is not included. In use, after the label 216 is filled out, signed, and removed from the container 212, the container can be opened to start the case without additionally having to remove a separate lock member.

Turning now to FIG. 16, there is illustrated a surgical system 310 according to a fourth example embodiment of the present invention. The system 310 is similar to that of the first embodiment, having a container 312 with a bottom 318 and a top 320, and a lock mechanism 314 with a lock member 324 received in two alignable lock openings 326 and 328. In this embodiment, however, the lock member is a plastic tie wrap or a twisty tie, and the alignable lock openings 326 and 328 are defined in tabs extending from the exterior of the container. In addition, the system 310 may include a spare tie 324 for relocking the container 312 after use for safe disposal. In an alternative embodiment, the lock mechanism is provided by a conventional slide-lock or snap-lock mechanism similar to that of commercially available surgical sharps boxes.

Turning now to FIGS. 17 and 18, there is illustrated a surgical system 410 according to a fifth example embodiment of the present invention. The system 410 is similar to that of the second embodiment, having a container 412 for surgical implements and a confirmation and/or signature label 416 for use and removal just prior to starting the surgery. In this embodiment, however, the lock mechanism is provided as a wrapper 414 with the label 416 on it. The wrapper 414 is preferably made of a clear plastic material and has a circumferential opener strip 415a with a pull tab 415*b* formed into it, similar to the wrapper, opener strip, and red pull tab on some conventional compact disc cases. The label 416 is preferably positioned on the wrapper 414 over the pull tab 415 so that when the label is peeled off, the pull tab 415*b* is pulled and the opener strip 415*a* is pulled to partially open the wrapper. The label 416 can be sized and shaped so that it wraps all the way, or most of the way, around the container 412, so that in order to remove the wrapper 414, the label must first be removed, thereby prompting the pause for the pre-operative assessment.

In the embodiments described herein, all of these components are sterilized so that the surgeon can sign the label at the operating table immediately prior to starting the surgery. To maintain the wrapper in sterile condition, a removable outer wrapper 478 is preferably provided that encloses the sterile components, as shown in FIGS. 17 and 18.

In other example embodiments, the system is provided with a container for surgical implements and a confirmation and/or signature label removably attached to the container, but without a lock mechanism for the container or with a lock mechanism that is not covered by the label. Instead, the label is positioned directly or indirectly on the container to merely impede opening the container; that is, the label is in a prominent position so that it is not easily overlooked and it thereby prompts the surgical team to conduct the pre-operative assessment. Such embodiments are provided by the first example embodiment modified without the lock mechanism, and the fourth example embodiment modified with the label on the container top only.

In still other alternative embodiments, the system includes a container with a scalpel (or other surgical implement) in it, with another way of forcing a pause without filling out a label. For example, the system can include a lock mechanism for the container that by itself forces the pause. The lock can be a small combination lock, with a combination that only the circulating nurse knows. The doctor and scrub tech confirm that they have the right patient and the right operation, and relay that information to the circulating nurse, who then confirms the information and gives them the code to open up the combination lock.

Referring to FIGS. 19A-25, an alternative embodiment of a surgical system in accordance with the present invention is described. The surgical system 500 has many similarities to that of the above-described embodiments. The surgical system 500 contains a container 512 which is preferably adapted to be trackable and/or can electronically communicate with other components of the system 500. The ability to be trackable and/or electronically communicate with other components of the system 500 allows the users of the surgical procedure the ability to continuously monitor and check that the scheduled surgical procedures for a patient is correct, thereby extending the prevention of wrong site surgeries to multiple patient-medical representatives interactions.

The container 512 has a top 514 and a bottom 516 secured together to provide an interior compartment. The interior compartment is designed to hold surgical instruments, such as described in FIG. 4, 10, or 11. The interior compartment is designed to hold pre-loaded surgical instruments specific for each surgical procedure. As part of the system 500, one or more labels, similar to the labels as described previously, for example label 16 described and illustrated in FIG. 8. The label must allow at least the surgeon, or other surgical team members, to fill in the surgical-site information within an input field of the label, i.e. the surgical-site information to conduct a pre-surgery assessment confirming the correct surgical site.

The container 512 has a locking mechanism, illustrated herein as a pin member 518 sized and shaped to slidably engage and/or be positioned within the top 514 where at least a portion of the pin member 518 is secured within an opening positioned within the bottom 516, as described in FIG. 4-6. Alternative mechanisms for locking the container 512 may include conventional slide-lock or snap-lock mechanism similar to that of commercially available surgical sharps boxes or other previously described mechanisms. Whatever mechanism locks the container 512, the label must cover and/or prevent the locking mechanism from opening prior to the removal of the label. To aid the user in signing the label, the top 514 of the container 512 may contain a recessed holding area 520 sized and shaped to hold a writing utensil, such as a pen 522. To retain the pen 522 within the recessed holding area 520, a writing utensil locking member, illustrated herein as two parallel and spaced apart finger-like extensions 524 and 526, are secured to the bottom surface 527 of the recessed holding area 520. The finger-like extensions 524 and 526 have some elasticity so that when the pen 522 is inserted between the two finger-like extensions 524 and 526, both move apart. Once the pen 522 is fully inserted within, the finger-like extensions 524 and 526 snap back to their original position, securing the pen 522 in place.

To allow for monitoring and/or tracking, positioned on or with the container 512 is a tracking and/or monitoring mechanism using, for example, a data capture and/or display device or system or other digital information options, illustrated herein as a bar code (an optical machine-readable representation of data) 528 preferably a Universal Product Code (UPC). The UPC can be programmed with various patient identifying information similar to that of the labels described previously, including the patient name or other identification means, type of surgery, site of surgery, and physician name. As such, when a physician or medical support team member scans the bar code 528 with a bar code reader or scanner, they will be able to view the information. Alternatively, the container may use a two dimensional bar code, such as a Quick Response Code (QR code), which is adapted to be read by an imaging device, such as a camera.

Figure 21:
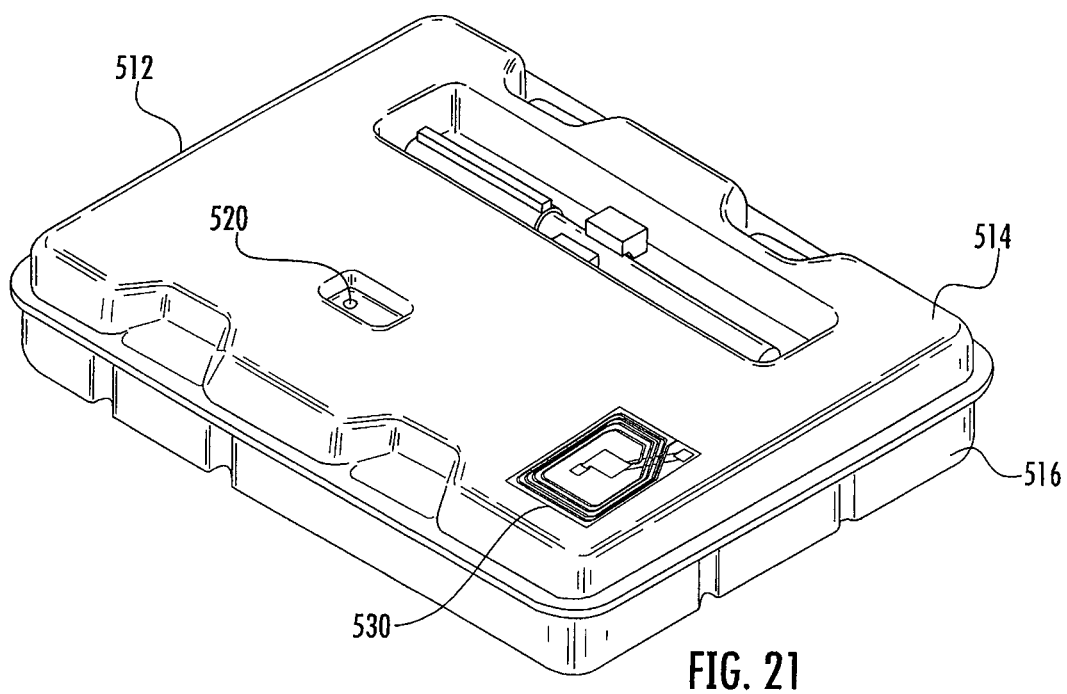
FIG. 21 is a perspective view of a container for surgical equipment according to an alternative embodiment of the invention, showing the container having an RFID transponder.

Referring to FIG. 21, the container 512 is shown using an alternative embodiment of a tracking and/or monitoring mechanism using, for example, a data capture and/or display device or system, illustrated herein as a radio-frequency identification (RFID) transponder 530. The RFID transponder 530 generally comprises a chip for storage and/or processing, an antenna for transmitting and receiving information, and an inlay for supporting the chip and antenna. While any RFID transponder known to one of skill in the art may be used, the RFID transponder 530 may be an active tag having a battery which runs the microchip circuitry, or a passive tag without a battery and using a RFID reader which is designed to send electromagnetic waves to induce the tag's antenna to power the microchip circuitry. The transponder 530 may be a read-only tag which contains data pre-written thereon, a write-once tag which allows the user to write data to the tag one time, or a full read and write tag which enables the user to write new data to the transponder as needed.

The inlay may be a substrate film which can support and hold the chip and antenna. Alternatively, the inlay can be a label or tag having self adhesion coating to ensure that the RFID chip and antenna adhere to a surface. The inlay may be embedded in plastic castings or casted in polyurethane resin coatings.

Figure 22:
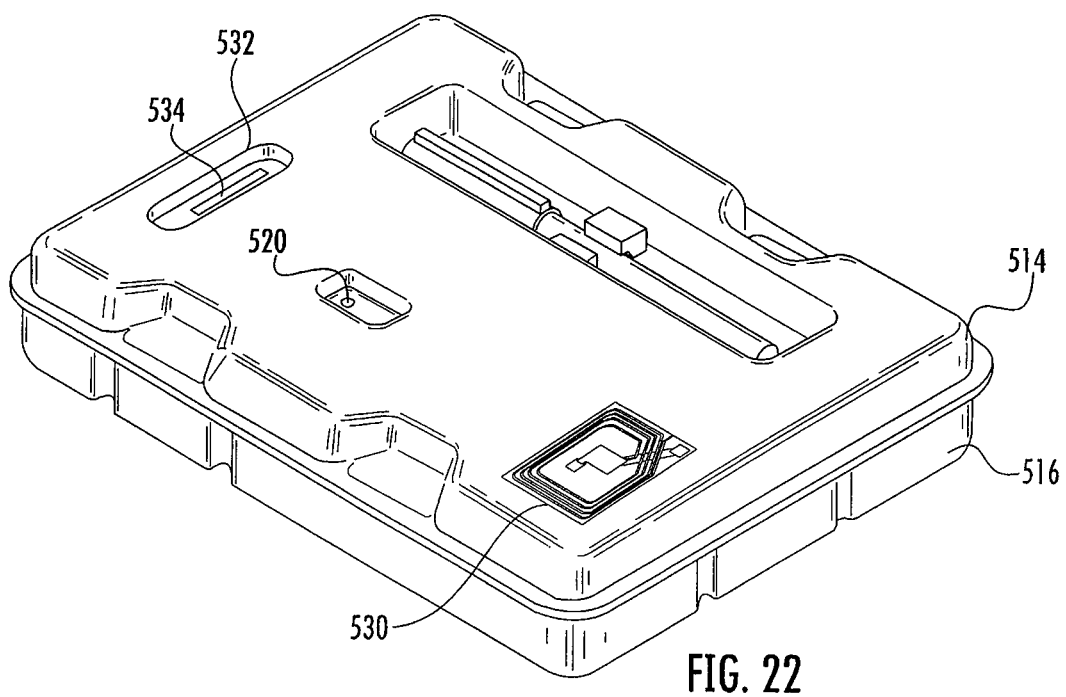
FIG. 22 is a perspective view of a container for surgical equipment according to an alternative embodiment of the invention, showing the container having a data storage device.
Figure 23A:
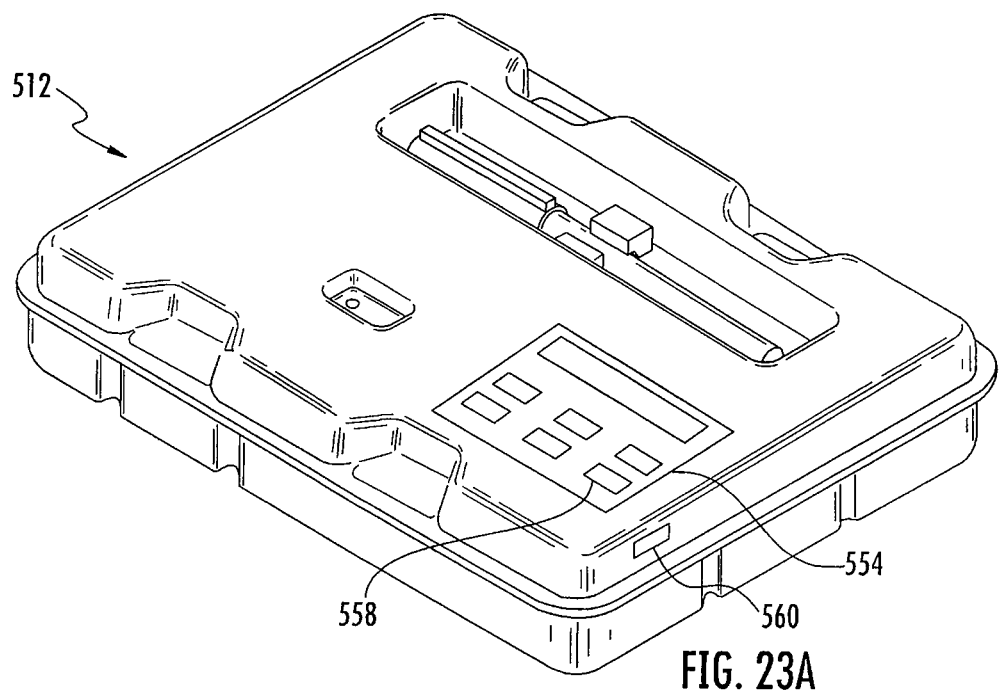
FIG. 23A is a perspective view of a container for surgical equipment according to an alternative embodiment of the invention; showing the container having a central control unit.
Figure 23B:
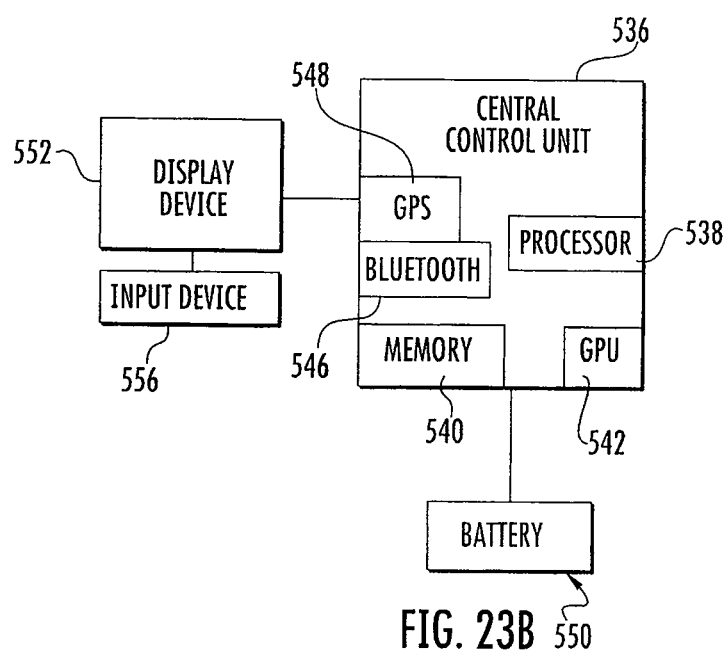
FIG. 23B is a schematic diagram of the components of an illustrative example of a central control unit.

FIGS. 22-25 illustrate examples of the container 512 having additional features. FIG. 22 shows the container 512 having an additional recessed storage area 532 adapted to store a data storage device, illustrated herein as a flash drive 534. The flash drive 534 preferably contains information relating to the patient that can be transported wherever the container 512 travels, i.e. from the initial pre-op discussion to the surgical room. FIGS. 23A and 23B illustrates a container 512 converted to a "smart" container. The top 514 is adapted to include a central control unit 536 including, for example, a processor 538, memory 540, graphic processing unit 542, GPS functioning 544, and Bluetooth wireless capability 546. The central control unit 536 can be powered by a battery 550 and electrically connected to a display unit 552, such as an LED screen 554, see FIG. 23A. Data input devices, such as buttons 558 or a keyboard (not shown), may be included to allow the user to input data. The container 512 may also contain a connection point, illustrated herein as a USB port 560 to allow for transfer of data from the central control unit 536 to a flash drive or a computer system via cables.

Figure 24:
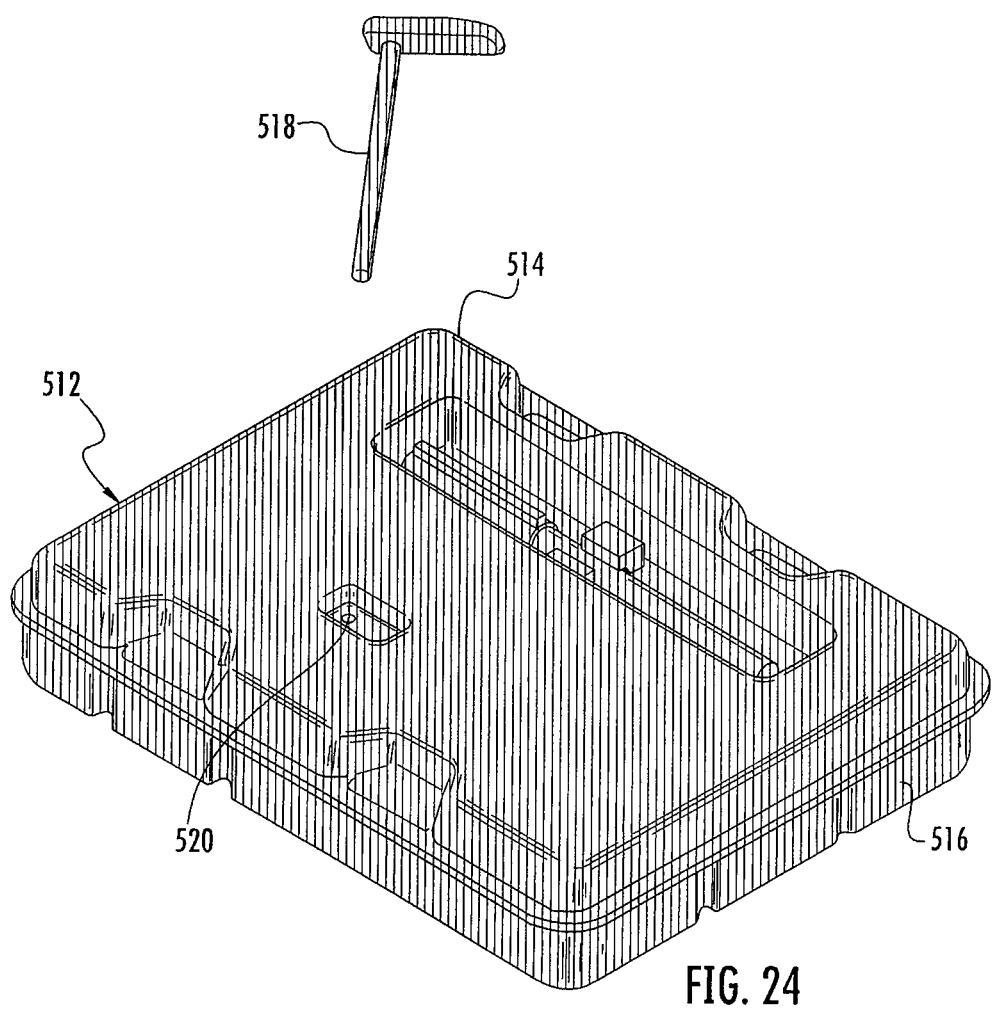
FIG. 24 is a perspective view of a container for surgical equipment according to an alternative embodiment of the invention, showing one embodiment of a surgical site visual indicator.
Figure 25:
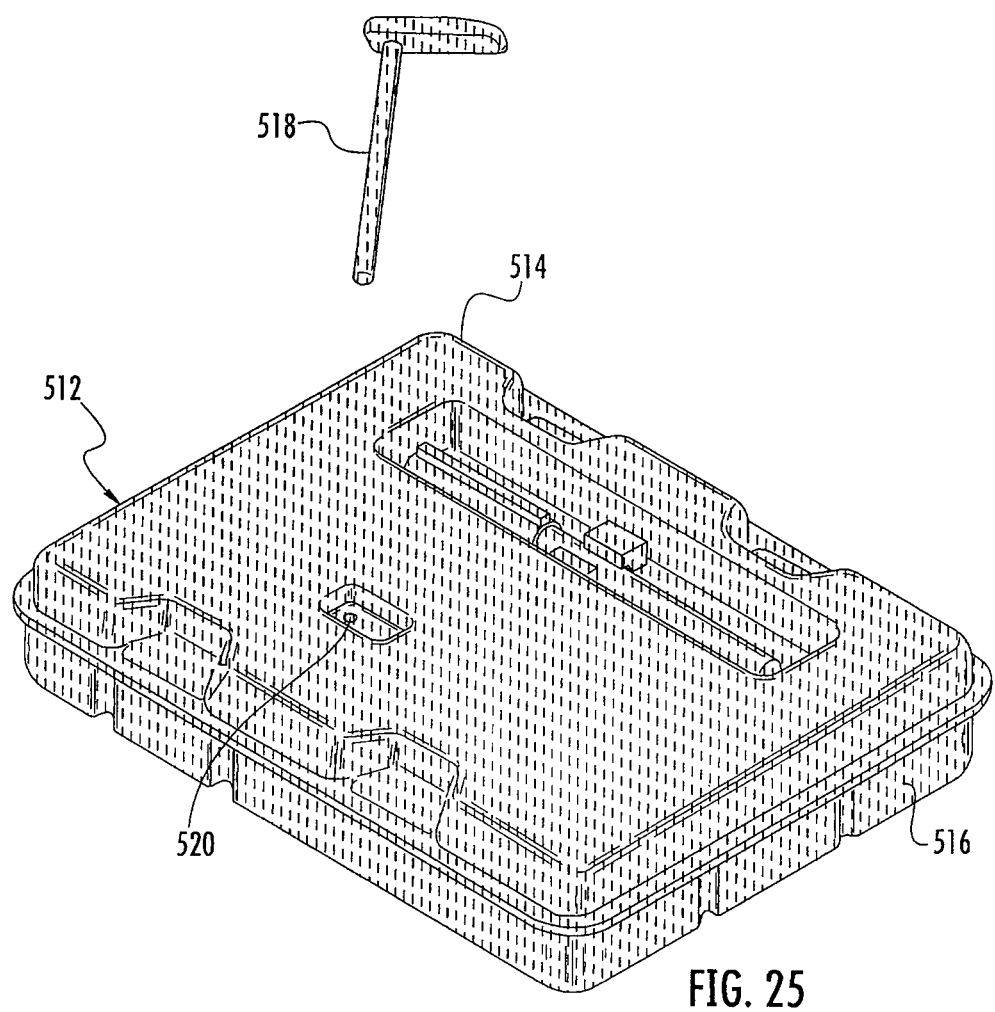
FIG. 25 is a perspective view of a container for surgical equipment according to an alternative embodiment of the invention, showing an alternative embodiment of a surgical site visual indicator.

FIGS. 24 and 25 illustrate rapid identification features of the container 512. As part of the overall surgical system 500, the containers are designed to provide easy and rapid visualization using a visual indicator to alert the surgical team as to which side (left or right), sometimes referred to as "laterality", of the patient a surgical procedure is to take place. As shown in FIG. 24, the container 512 includes all or at least a portion of the top 514, the bottom 516, and the locking pin 518 having a color coding of some shade of red, illustrated herein as pink/rose color hash markings, to indicate a right side surgical procedure. The locking mechanism is preferably colored as well. FIG. 25 illustrates the container 512, and locking pin 518, having a left side surgical procedure indicator, illustrated as a purple based color, see broken line hatchings, preferably a lavender color. Alternative visual indicators may include symbols, letters, words or phases. In any embodiment, the surgeon or surgical team member can easily ensure that the position of the surgical site or laterality aligns with the color of the container 512.

Figure 26:
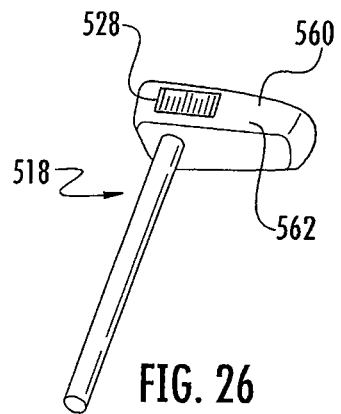
FIG. 26 is a perspective view of an embodiment of the locking pin member containing a data capture and/or display device.
Figure 27:
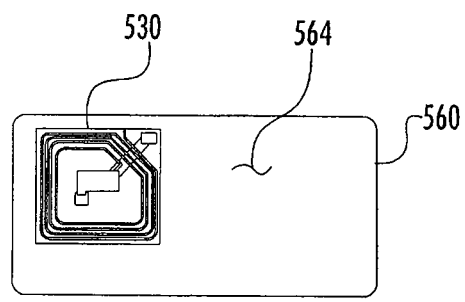
FIG. 27 is a top view of an embodiment of the locking pin member containing an alternative embodiment of a data capture and/or display device.
Figure 28:
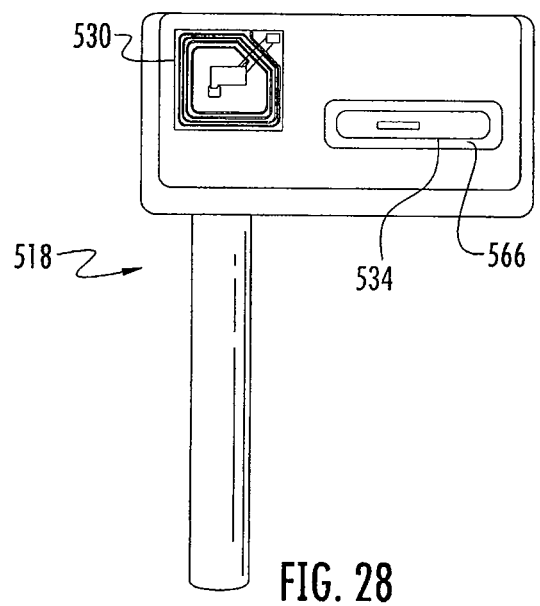
FIG. 28 is a perspective view of an embodiment of the locking pin member containing a data capture and/or display device and flash drive.

FIGS. 26-28 illustrate the pin member 518 adapted to contain additional features that enhance the tracking and/or can electronic communication with other components of the system 500. As illustrated in FIG. 26, the tab 560 contains a bar code 528 secured to the side surface 562. FIG. 27 illustrates a top view of the pin member 518 showing an RFID transponder 530 secured to the top surface 564. FIG. 28 illustrates the pin member 518 having a tab recessed receiving area 566 sized and shaped to receive a data storage device such as flash drive 534.

With the ability to track and/or communicate with other components of the surgical system, the container 512 can be used in multiple time periods within the entire surgical procedure, including pre-hospitalization/surgical period, the day of pre-surgical procedure in the pre-op holding area, and the actual operating room. The systems, devices and methods in accordance with the present invention are designed to prevent wrong patient, wrong site, wrong side surgery by providing multiple steps of protection at multiple time points when the patient is passing through the surgical procedure environment, see FIGS. 29A and 29B. As described herein, the use of the term "surgical procedure environment" or "surgical procedure" defines any period when the patient is interacting with his/her medical team or medical team associates including but not limited to office personnel, nurses, medical technicians, surgeons. The time period of interaction includes pre-hospitalization and hospitalization, including pre, post and during a surgical operation. The term may also include personnel involved with final data collection points such as a patient's insurance company, federal agency programs, such as Medicare/Medicaid that disburses funds to the hospital as a method of payment or any other agency, private or federal, which generates payment to the patient or patient's hospital for the specific surgical case.

Pre-Surgical Booking

Ensuring the prevention of wrong site surgeries begins as early as the initial steps of the surgical procedure. At the time of surgical booking, errors can be initiated and perpetuated all the way through the actual surgical procedure. The system and methods of the present invention start when the surgeon's office schedules the surgery with the patient, see step 610. At the time the surgery is scheduled by the hospital, the patient's name and information are associated with a container, preferably a trackable one such as container 512.

The container 512 may be provided with a unique container identification number, similar to a vehicle identification number (VIN) used for automobiles. The container identification number (CIN) may be established at the time of manufacture and remains with a particular container. This number is unique to the container in that the number is never reused and never applied to different containers. The unique identification numbers can be integrally formed into the container or may be attached to the container as part of a separate label, or part of the bar code or QR/Scan codes. Once the unique number is assigned to a container and/or is then further correlated or associated to a particular patient, the container as well as the patient information coupled to it is serialized. This allows for the container to be tracked and analyzed as it moves through the medical system. In cases in which a patient has been determined to have wrong information, i.e. the patient should have a right side surgery, but the box is coded for a left side surgery, the container is destroyed and the reason(s) for its destruction is electronically attached to the unique number. This allows for hospitals or manufactures to review all containers manufactured or scheduled for a medical procedure to determine how many were actually used in such surgical procedures. For those containers not used, reasons as to why containers failed to be used in a medical procedure, potential errors (incorrect/inaccurate manual inputs), or wrong site surgeries/never events can be reviewed, providing insight as to when, where, and why surgical mistakes were made. Periodical reviews of such data allows hospitals to identify areas that need improvement.

If the patient is undergoing a surgical procedure which requires the surgeon to perform a procedure on a particular side, a color coded container 512, such as those described in FIGS. 24 and 25, is associated with the patient, see 614. For surgical procedures that do not require laterality, the container 512 will be a neutral color, such as gray.

Alternative embodiments of the medical system 500 may include the use of a non-sterile outer box 521, see FIG. 19B having an upper portion 523 securable to a lower portion 525 which houses the container 512. Preferably, the outer box contains tracking and/or electronic communications mechanisms, such as a bar code (including a QR code) or RFID tag. The outer box 521 may also be color coded to match the color of the container 512. In this manner, the container 512 can be transported to various locations and/or handled by the surgical team while on route to the operating room without concerns of contamination. In addition to color coding or matching, various patient related information, such as for example the patient's name, history, surgical procedure, side of surgery, associated color coding is encoded to an identifying label or tag label, such as a bar scan.

At the time of the surgical procedure, the container 512 is delivered to the patient at the pre-operation holding area, see 618. At this point, numerous opportunities are available to confirm that the patient will undergo the correct surgical procedure at the correct site, see 620. When the surgeon visits with the patient to discuss the surgery, and possibly mark the site of surgery, the surgeon 622A and the patient 622B and will confirm the site of surgery. Additional surgical team members may also perform surgical procedure checks. For example, the prep nurse 622C, and the operating room nurses 622D, may confirm the patient's information is correct by matching the patient information to the information of the scan bar. As such, the surgeon 622A, prep nurse 622C, and the operating room nurses 62D may scan the bar code using a bar code (including a QR code) reader.

If the information matches, the patient continues with the medical procedure process. As part of the system 500, when a scan of the bar code/QR code is performed, the information may be displayed (i.e. surgical procedure for right side would be displayed with at least a rose color that matches the rose color of the container 512) with a matching color background so that the medical professionals can easily, quickly visually confirm laterality. Determining or confirming surgical procedures and/or location at this point prevents any mistakes made at the surgeons' office or by the hospital scheduler when scheduling the procedure. In addition, all members of the surgical team are aware of what procedure needs to be performed on the correct patient, and on what side the procedure is to occur. If the surgeon or surgical team member determines the surgery was not scheduled correctly, a new container 512 with the correct information will be ordered and brought back to the pre-operation holding area, see 624.

Once the patient information has been determined to be correct, he/she will be transferred to the operating room. At this point, the patient will be checked in, see 626. At check in, patient information is verified and may be checked against the bar code information of the container 512, see 628. The operating nurse will put in the information in the electronic health record, see 630. Such step could be performed at a check in or sign in period. This information must match the information already in the electronic health records. If any information is incorrect, the electronic health record can be put on hold, or on "freeze" so that any individual accessing the record would know that the patient must not undergo any surgical procedures, see 632 and 634.

Once a determination has been made the information matches, i.e. it is the correct patient, it is the correct surgery and correct surgical site, container 512 is presented to the surgeon, see 636. If the container 512 is placed in an outer box, the surgeon simply removes the outer box and opens container 512. In either case, once the patient is prepped and draped, a formal and final timeout is performed by the members of the surgical team, see 638. The surgeon fills in the label, see 640, either a label such as 16 or scans the bar code 530, placed over the locking mechanism of container 512 and pulls it off, see 642. The system 500 can be adapted to allow the surgeon to perform electronic signatures, which can then be transferred to the patient's chart. If the container 512 contains a flash drive or other memory storage device, the surgeon or nurses could use such device to match the patient information in the electronic health record. If any information does not match, a freeze could ensue, warning those involved with the surgery to stop any further proceedings. He/she can now open the container 512 to gain access to the surgical equipment therein and begin surgery, see 644.

Figure 29C:
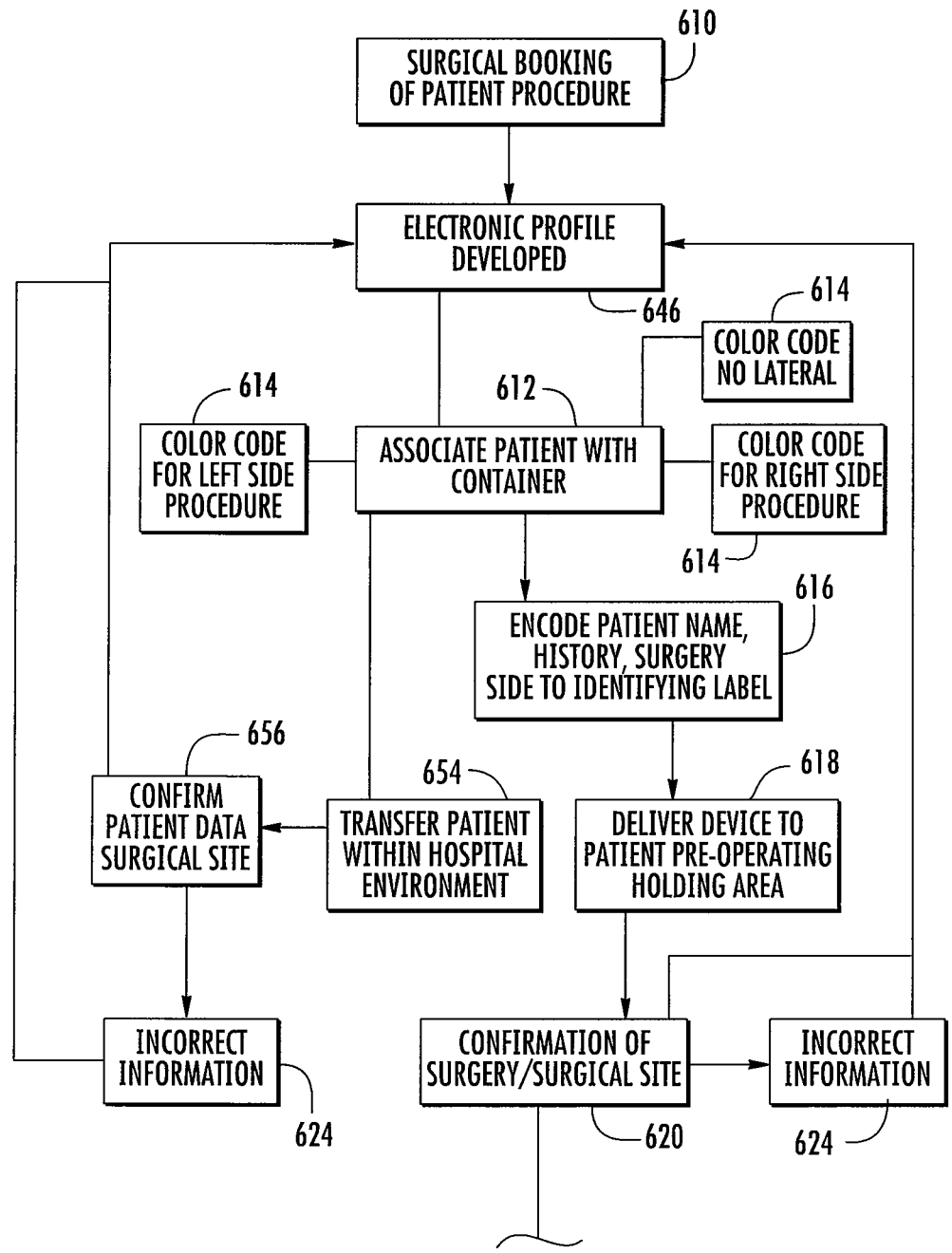
FIG. 29C and FIG. 29D illustrate a flow chart describing an representative embodiment of a method of preventing and tracking a wrong-site error during surgery in accordance with the present invention.
Figure 29D:
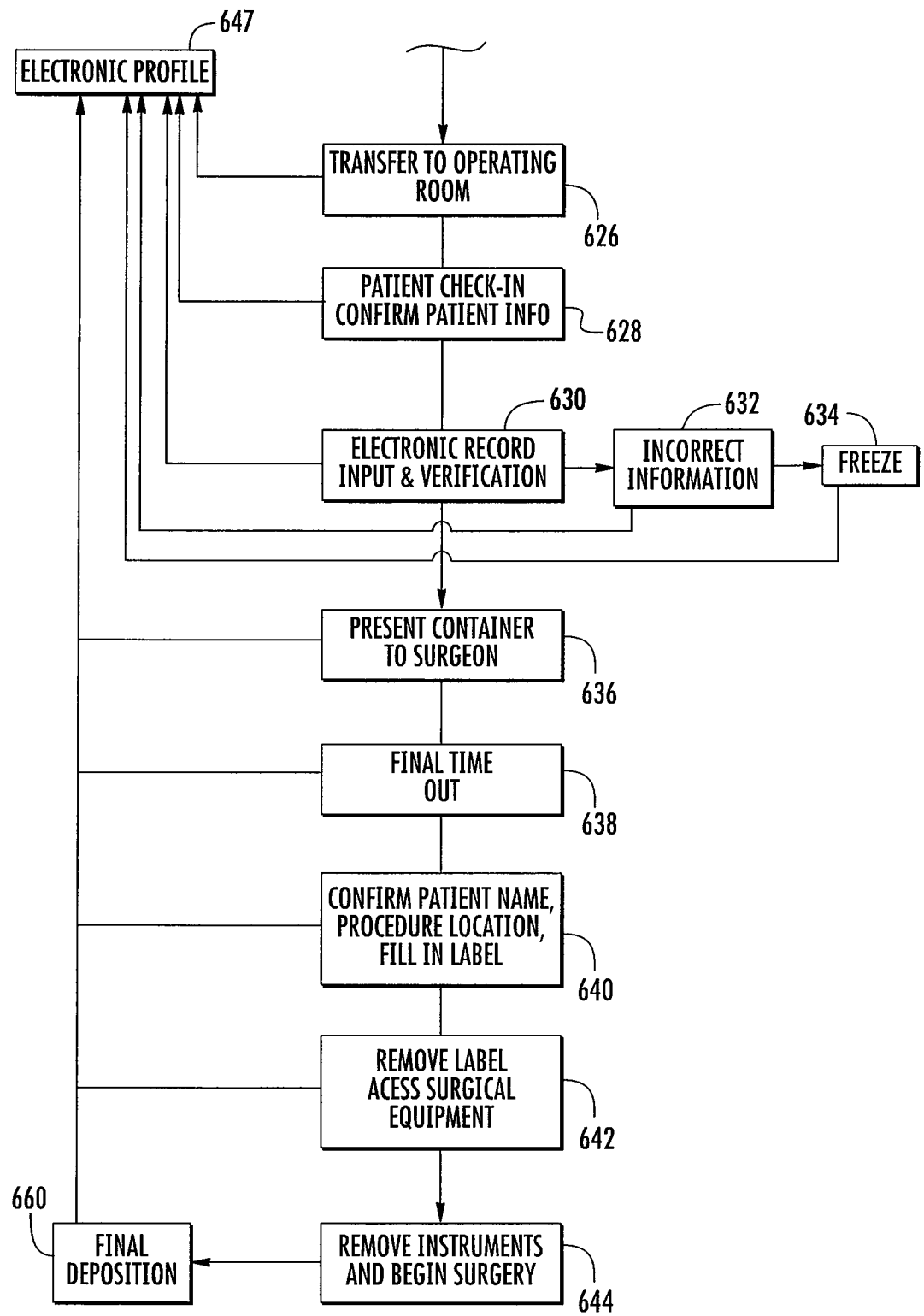

Referring to FIG. 29C and FIG. 29D, a representative embodiment of a method of preventing and tracking wrong-site surgery near misses and wrong-site surgery errors, prior to, and during surgery, is described. Wrong-site surgery near miss and error data is collected to improve tactical decisions prior to surgery. As defined herein, "near miss data" refers to patient information that does not match with the patient procedure. Such information can be a determination of wrong side of surgery, wrong site of surgery, or wrong patient. Such wrong information was determined before an actual procedure was done on the wrong side of surgery, the wrong site of surgery, or on the wrong patient. Any surgical container (and its unique identification number) discarded as a result of a determination of the wrong side of surgery, the wrong site of surgery, or on the wrong patient wall be tracked and noted as part of the near miss data. Pauses, or stopping of a procedure and correcting missing information can be tracked and included as near miss data. The system and methods described herein, produce, capture, or store mineable electronic wrong site surgery near miss and error data to support hospital system analysis and process improvement, in order to systematically decrease wrong site surgery errors across hospital systems and organizations. The method described utilizes many of the same steps as described in FIGS. 29A and 29B (with like reference numbers indicating the features of the steps described previously) with the additional benefits of capturing wrong-site error data as a patient interacts or moves with the surgical procedure environment. Accordingly, in combination with one or more of the previously described steps, the method of preventing and tracking wrong-site errors during surgery utilizes one or more of 1) patient biometric identifiers, 2) surgical container identifiers, 3) container tracking, preferably linked to container identifiers, and 4) near miss wrong site surgical mistakes. As such, the method and system is designed to track and record events (patient scheduling, moving within the hospital system, time outs, incorrect information) and preferably electronically exports, such as information and patient outcome, to a digital or paper wrong site surgery record. The methods and systems utilized may include various technologies, such as biometric readers, cameras, sensors, and tracking devices positioned within the surgical procedure environment to electrically capture various information as the patient moves within the system.

Information obtained by the electronic data created is used to provide a wrong site surgical procedure electronic patient profile which can be used to identify when, where, or how a wrong site surgery occurred. Review of the data captured ensures key attributes of performing the correct surgery and at the correct patient site is completed properly, including performing a time out prior to surgery.

Figure 29E:
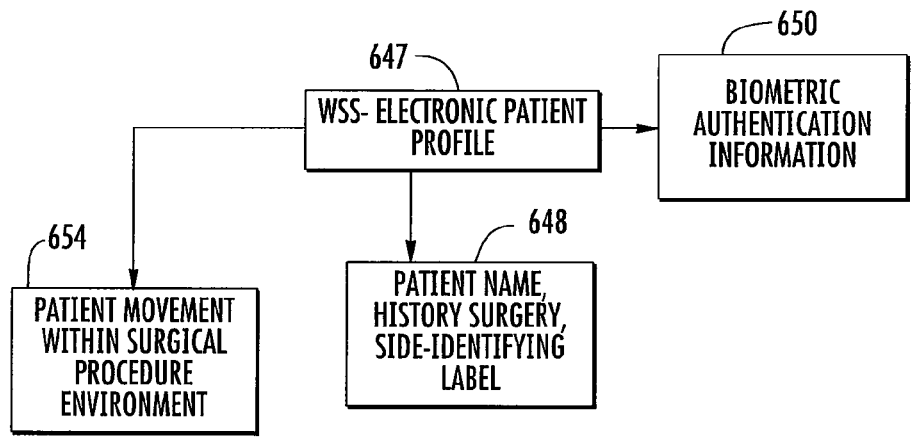
FIG. 29E is an illustrative example of one or more biometric components of a system for collecting data to provide or update a wrong site surgery electronic profile.
Figure 29F:
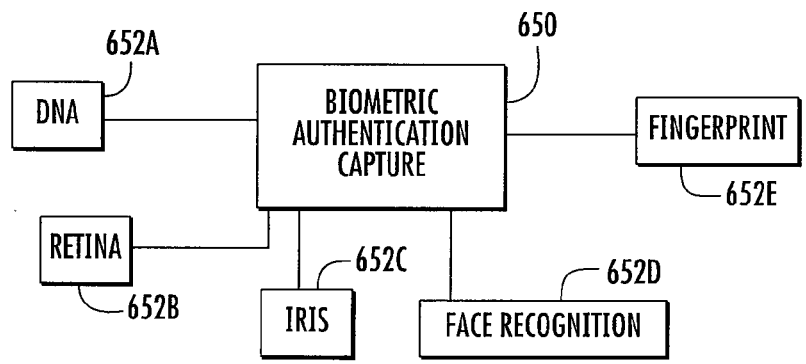
FIG. 29F is an illustrative example of the one or more components of a systems for collecting data of patients as he/she moves within a medical environment in order to populate and update a wrong site surgery electronic profile.

The system and methods of the present invention may start as early as when the surgeon's office schedules the surgery with the patient, step 610. A wrong site surgical electronic profile is created for the individual patient, see 646. The wrong site surgical electronic patient profile 647 contains all necessary information which identifies the patient, see 648 (FIG. 29E), including name, social security number, physical characteristics of height, weight, age, eye color, and hair color, as well as other information required for the surgical procedure including type of surgery, laterality of surgical procedure, and physician name. The wrong site surgical electronic patient profile 647 is designed to continuously be updated with information related to the patient as he/she moves from place to place. The wrong site surgical electronic patient profile 647 may be created and/or stored using a computer system having a micro processor, data storage, memory, input device, such as a keyboard, and a display unit, such as an LCD monitor. The wrong site surgical electronic patient profile 647 may also be displayed by other computer systems within the surgical procedure environment, such as in the operating room, at a nursing station, or at a patient's room. The wrong site surgical electronic patient profile 647 may further include biometric authentication information 650, such as but not limited to patient DNA 652A (see FIG. 29F), patient retina display images 652B, patient iris scan 652C, face recognition information 652D, fingerprint 652E, or combinations thereof. Additional information related to the patient's movement within the surgical procedure environment 654 (FIG. 29E) may be obtained and used as part of the wrong site surgical electronic patient profile 647.

Figure 29G:
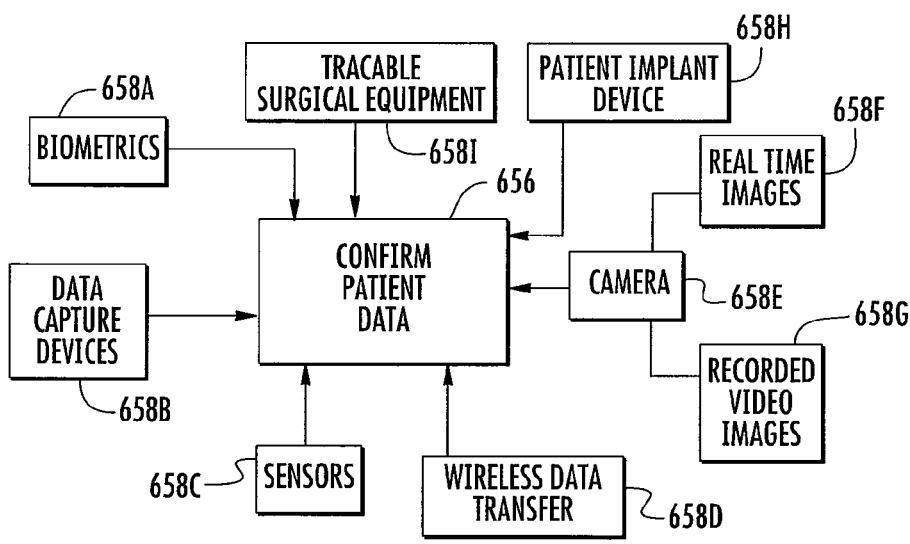
FIG. 29G is an illustrative example of the components that provide for data collection or patient data confirmation as the patient navigates the surgical procedure environment.

At the time the surgery is scheduled by the hospital, the patient's name, information, and surgical profile are associated with a container, see step 612, preferably a trackable one such as container 512. The assigned container 512 can be transferred with the patient from any point in the procedure to the operating room. Moreover, using tracking methods such as RFID or GPS tracking, the device can be monitored and tracked in real time so conformation that the box is with the patient at all times can be accomplished and documented. The step of associating color codes to the container, step 614, delivery of device to patient pre-op holding area, step 618, confirmation of surgical/surgery site, step 620, may be performed as described previously. Such information may be obtained and recorded as part of the patient's wrong site surgical electronic patient profile 647. For instance, confirmation of the surgical site, see 620, and any determination of incorrect information relating to the surgery, see 624, is recorded as part of the patient's wrong site surgical electronic patient profile 647. As the patient is transferred within the hospital setting, see step 654, confirmation of patient data related to the surgical site is obtained, see step 656, and preferably recorded as part of the patient's wrong site surgical electronic patient profile 647. FIG. 29G illustrates various mechanisms as to how patient data related to the surgical site is obtained or confirmed, including biometric data 658A using biometric devices (i.e. iris scans, device to obtain finger prints, data capture devices 658B, such as bar code scanners, sensors 658C, wireless data transfer systems 658D, such as RFID systems, or cameras 658E. The camera 658E may provide wrong site surgical electronic patient profile 647 using real-time images/videos 658F or recorded video images 658G. Patient implants, 658H, such as embedded chips within a patient body to identify the patient information, may also be used. Trackable surgical equipment tagged with tracking devices 658I, such as RFID chips, may be included as well. These devices or equipment may be positioned anywhere within the surgical procedure environment, and any information obtained therefrom forms the wrong site surgical electronic patient profile 647.

Once transferred to the operating room, see step 626, FIG. 29D, the method of preventing and tracking wrong-site errors during surgery includes one or more steps, steps 628-644, as described previously. One or more of steps 628-644 can be used to form part of patient's wrong site surgical electronic patient profile 647. For example, as the patient is transported to the surgical operating room and the information is confirmed, whether via visual inspection, biometrics, or data display or capture devices, all data obtained can be electronically transferred to the patient's wrong site surgical electronic patient profile 647. In addition, the final time out, step 638, performed by the surgeon can also be noted and electronically transferred to the patient's wrong site surgical electronic patient profile 647.

At each step of the process described in FIG. 29C and FIG. 29D, one or more members of the surgical procedure environment, i.e. surgeon, surgical staff, hospital staff, may manually or electronically enter decision of "GO" to indicate a specific step is to continue as all information and actions to be performed are correct at that specific step; a decision of "NOGO" to indicate that information and actions involved with that step have been identified as incorrect, or "PAUSE" to indicate there is incomplete information or it is unclear whether information and actions are correct. A "PAUSE" temporarily halts the process until information and actions are determined to be correct. An override may be used to continue. The process may be designed so that a "NOGO" or "PAUSE" indication freezes the patient's wrong site surgical electronic patient profile 647 until the situation is corrected, understood, or overridden.

Once the surgical procedure is complete, a final deposition, 660, to the patient's wrong site surgical electronic patient profile 647 may be entered. The final deposition 660 includes information related to final payment. This tracking point includes a patient's insurance company or federal program (i.e., Medicare), issues funds to the surgical center or disburses payment to the patient or patient representative, or in the case of wrong site surgical error, any compensation paid to the patient or settlement for damages associated with the wrong site surgery.

Figure 30:
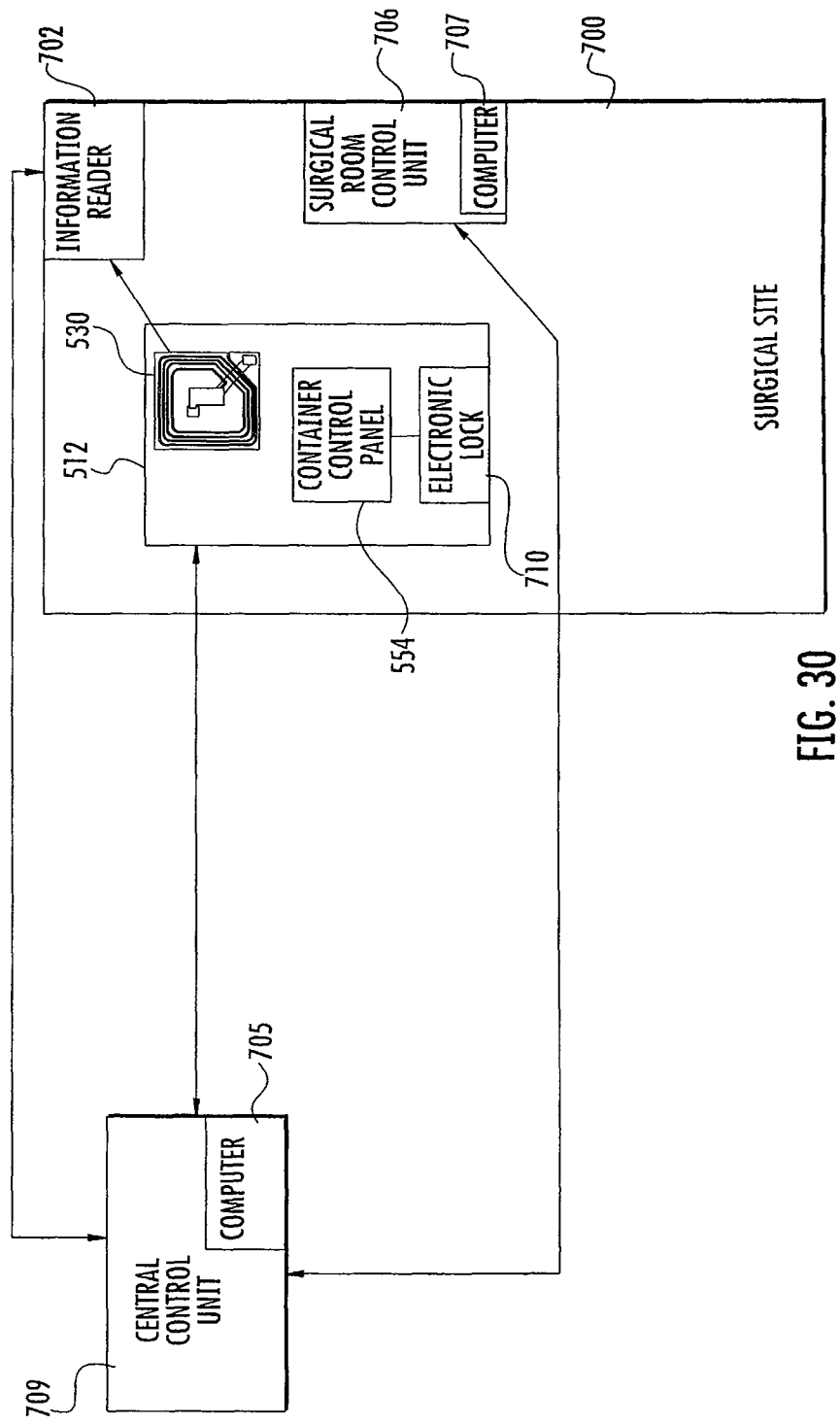
FIG. 30 is a schematic illustration of a surgical system which utilizes a surgical container in accordance with the present invention.
Figure 31:
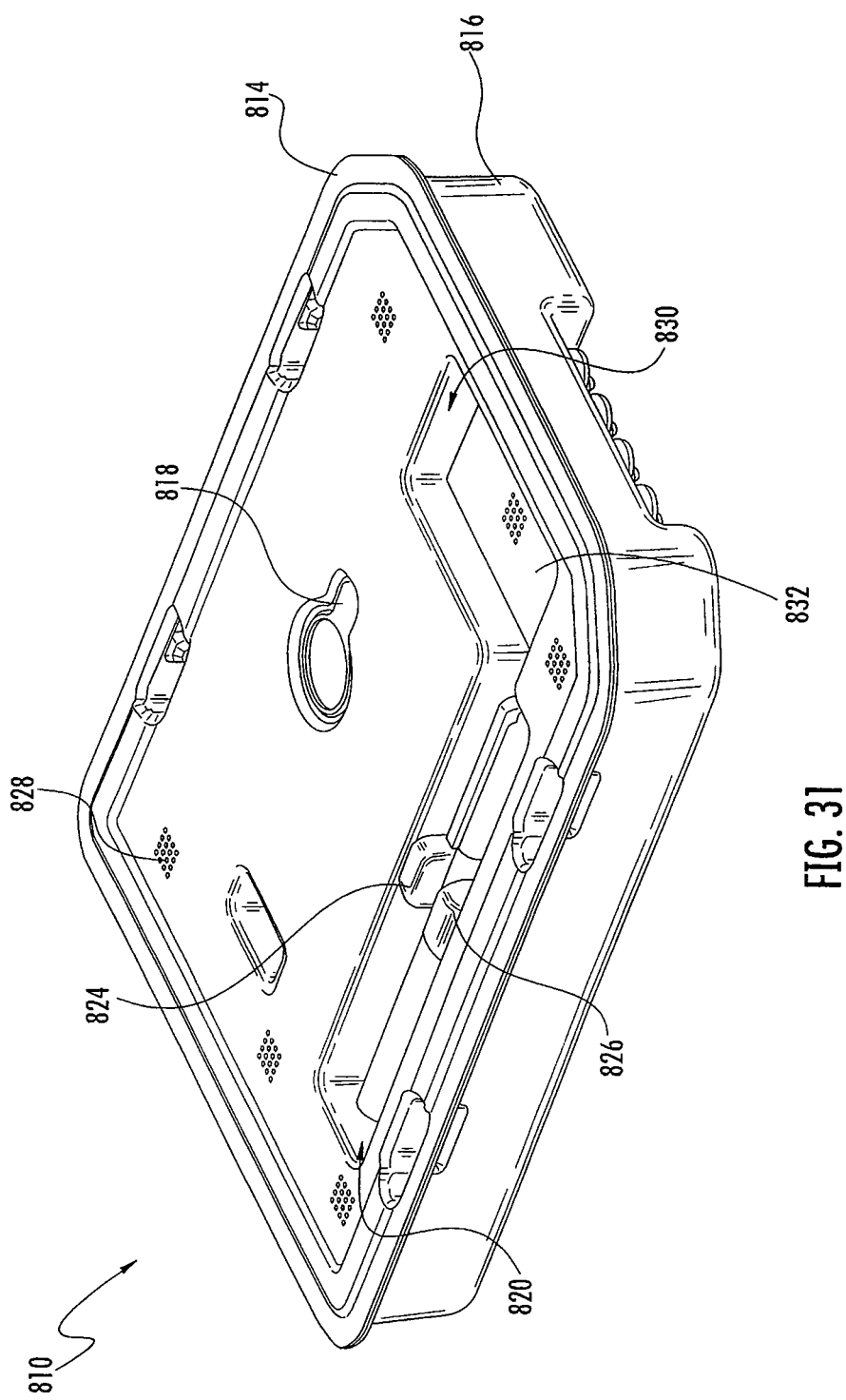
FIG. 31 is a perspective view of a container for surgical equipment according to an alternative embodiment of the invention.
Figure 32:
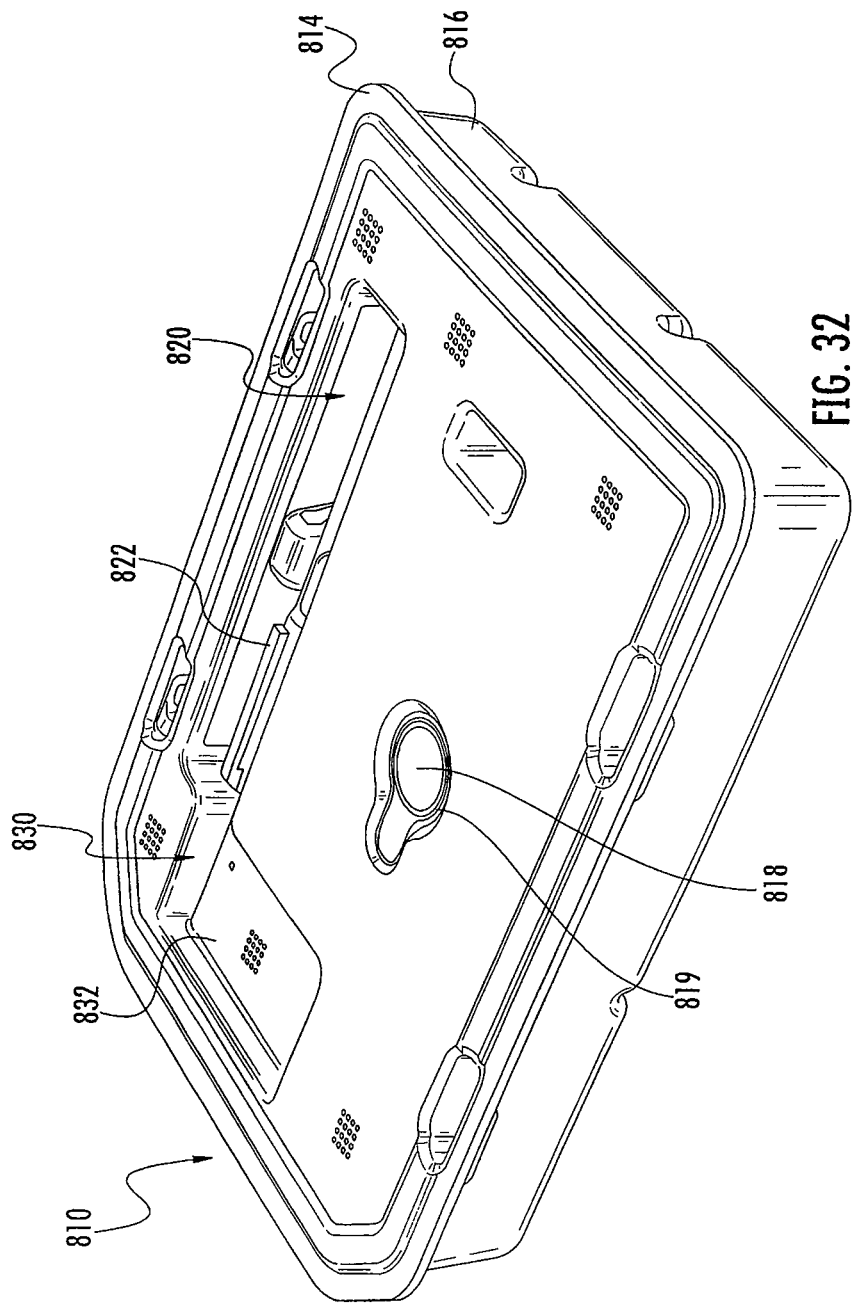
FIG. 32 is an alternative perspective view of the container illustrated in FIG. 31.
Figure 33:
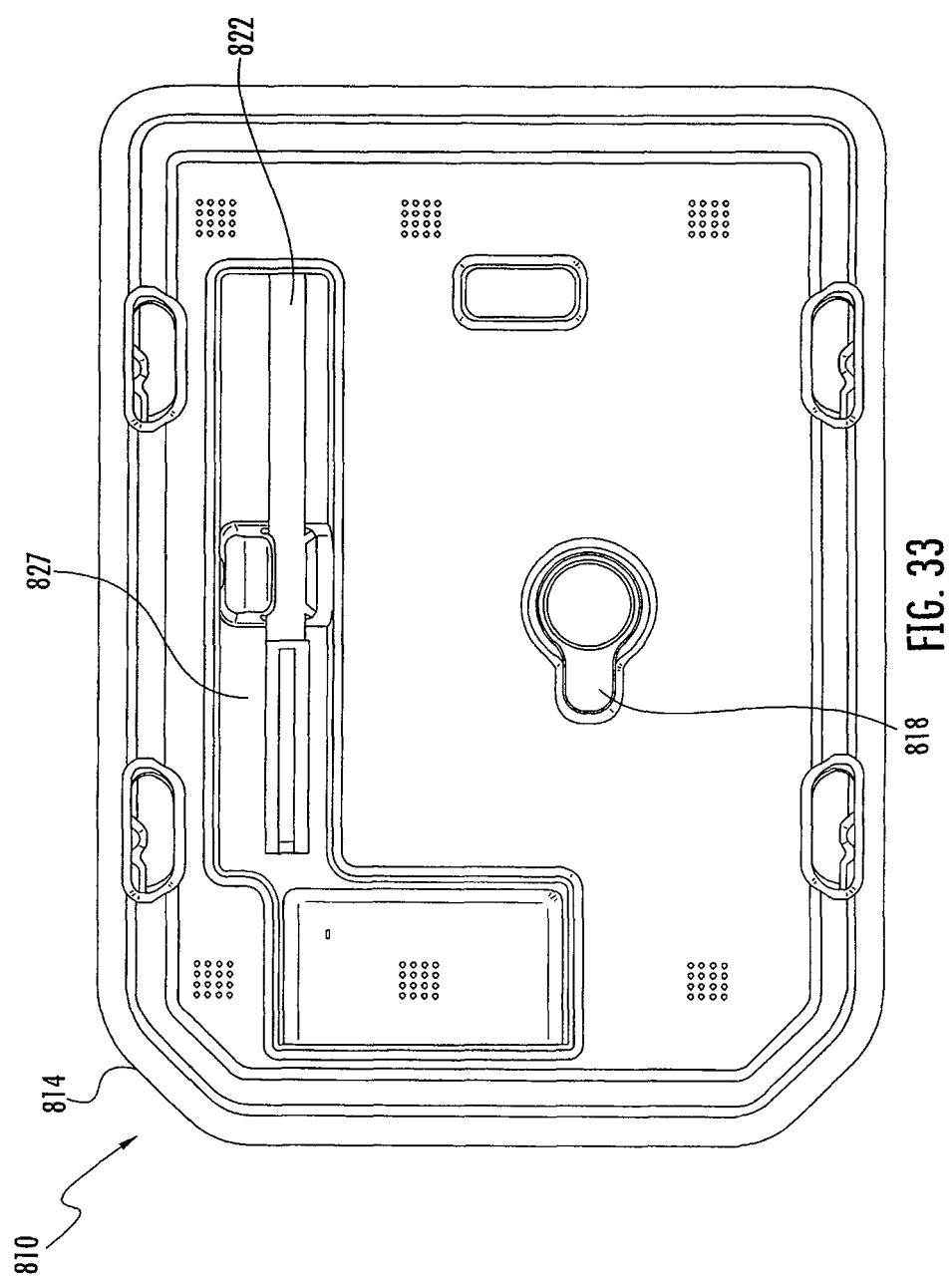
FIG. 33 is a top view of the container illustrated in FIG. 31.
Figure 34:
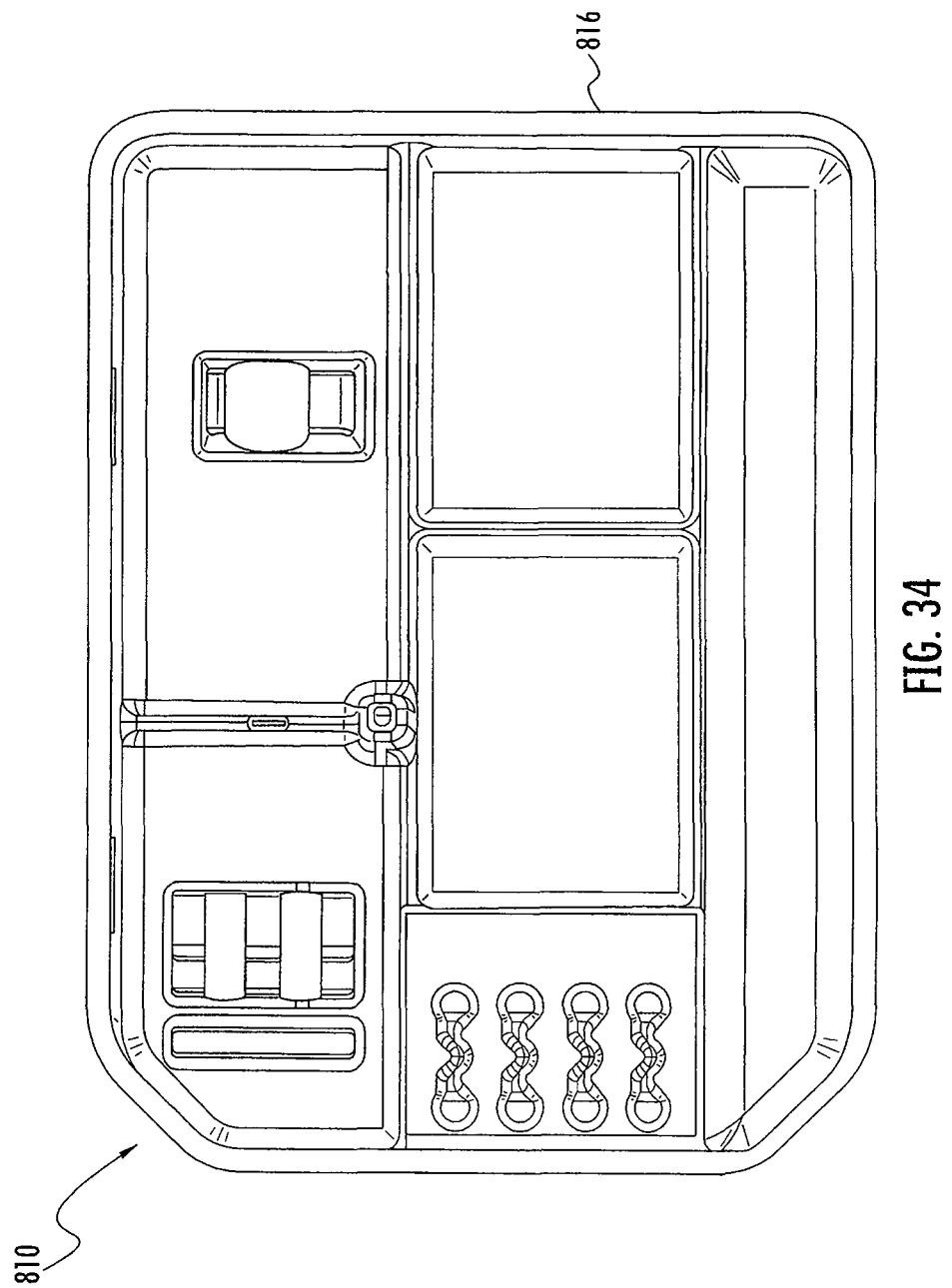
FIG. 34 is a bottom view of the container illustrated in FIG. 31.
Figure 35:
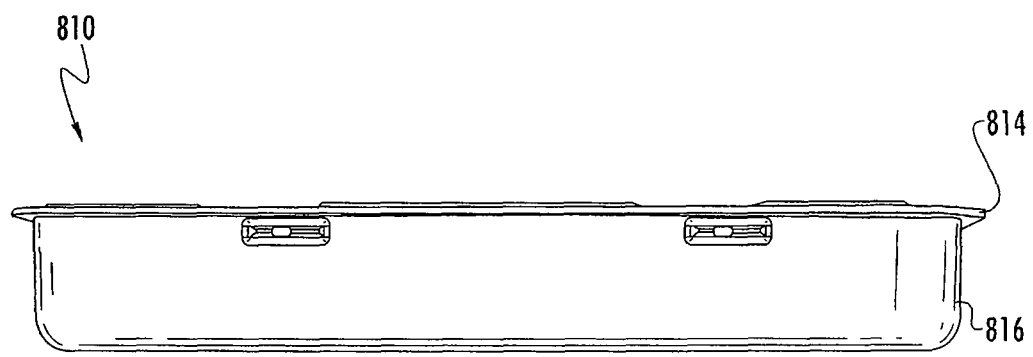
FIG. 35 is side view of the container illustrated in FIG. 31.
Figure 36:
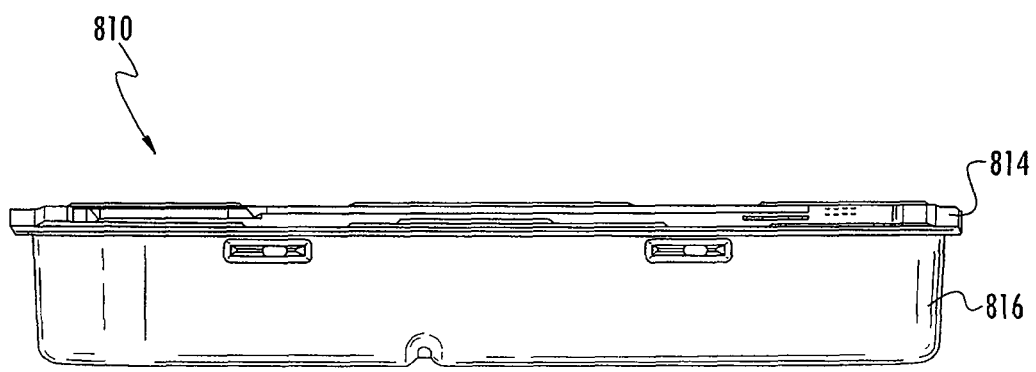
FIG. 36 is an alternative side view of the container illustrated in FIG. 31.
Figure 37:
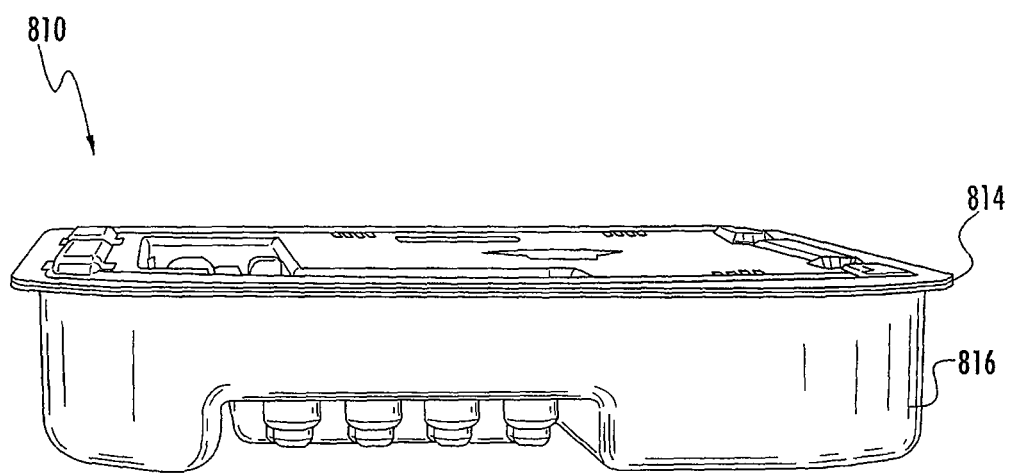
FIG. 37 is a front view of the of the container illustrated in FIG. 31.
Figure 38:
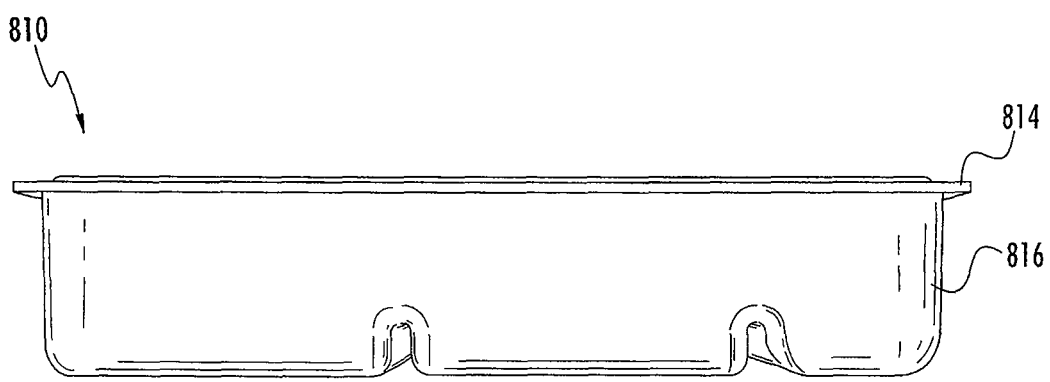
FIG. 38 is a back view of the container illustrated in FIG. 31.

Referring to FIG. 30, the present invention is shown linked to a smart surgery room. For example, the container 512 located in a surgical room 700 may contain a container control panel such as control panel 554. Within the surgical room 700, an information reader, such as a RFID reader 702 is located to read the RFID tag 530. The container control panel 554 is preferably electronically connected, via wired or wireless technology, to a hospital or central control unit 704 having one or central computers 705 outside the surgical room 700. The control unit could be a manned station functioning similar to a flight control tower. Alternatively, or in addition to, the container control panel 554 may be in electronic communication with a surgical room control unit 706 having at least one computer 707 located within the room. Individuals manning the control unit 704 may provide the surgeon within the surgical room 700 clearance to proceed with opening the container 512 based on the information received from the container, using, for example, a radiofrequency device. Based on the information received, the container may be opened remotely using an electronic lock 710 on the container 512. Preferably, the lock would be electrically coupled or in communication with the hospital control unit 704 and/or the surgical room control unit 706.

Additional features of the system may include container 512 and/or the surgical equipment having LEDs attached thereto to allow for tracking by optical or camera guided navigation systems. In addition to the above described features, it is understood that the container 512 may include or be adapted to include one or more features described previously, whether as part of a system or as a feature of a container embodiment.

In addition to providing a timeout, the medical system 500 allows for tracking of errors from pre-hospitalization to the actual surgical procedure. This provides a hospital valuable data as to where errors or possible errors may have occurred.

Accordingly, the present invention provides a number of advantages. In particular, the system and method of the invention insure a final confirmation of the correct patient, procedure, site, and as applicable, implants or instrumentation, is performed thoroughly and consistently, immediately prior to allowing incision to be made. The marking of the surgical site, the required use and removal of the confirmation checklist before accessing the surgical blades needed to start the surgery, and the resulting open communication between the patient, the surgeon, and the operating team, all contribute to reducing wrong-site medical errors. In addition, the surgical container provided by the invention can be used as a needle box for sharps disposal at the end of the case, and as a neutral zone during the case to decrease the incidence of needle sticks or lacerations from the surgeon and the surgical technician handing each other sharp instruments such as scalpels or needles. Furthermore, use of the invention can actually be extended to other areas of the hospital where an incision might be made, such as in the interventional radiology suite, the intensive care unit, or the emergency room.

Referring to FIGS. 31-38, an alternative embodiment of a container 810 is shown. The container 810 has a top 814 and a bottom 816 secured together to provide an interior compartment. The interior compartment is designed to hold surgical instruments, such as described in FIG. 4, 10, or 11. The interior compartment is designed to hold pre-loaded surgical instruments specific for each surgical procedure. One or more labels, similar to the labels as described previously, for example label 16 described and illustrated in FIG. 8, can be secured to the container 810. The label must allow at least the surgeon, or other surgical team members, to fill in the surgical-site information within an input field of the label, i.e. the surgical-site information to conduct a pre-surgery assessment confirming the correct surgical site.

The container 812 has a locking mechanism, illustrated herein as a pin member 818, similar to pin 518, sized and shaped to slidably engage and/or be positioned within the top 514 where at least a portion of the pin member 818 is secured within an opening positioned within the bottom 516, as described in FIGS. 4-6. A ring 819 is secured to or integrally formed to the pin member 818, acting as a mechanism for grabbing and pulling the pin member 818 out. Alternative mechanisms for locking the container 812 may include conventional slide-lock or snap-lock mechanism similar to that of commercially available surgical sharps boxes or other previously described mechanisms. Whatever mechanism locks the container 812, the label must cover and/or prevent the locking mechanism from opening prior to the removal of the label.

To aid the user in signing the label, the top 814 of the container 812 may contain a recessed holding area 820 sized and shaped to hold a writing utensil, such as a pen 822. To retain the pen 822 within the recessed holding area 820, a writing utensil locking member, illustrated herein as two parallel and spaced apart finger-like extensions 824 and 826, are secured to the bottom surface 827 of the recessed holding area 820. The finger-like extensions 824 and 826 have some elasticity so that when the pen 822 is inserted between the two finger-like extensions 824 and 826, both move apart. Once the pen 822 is fully inserted within, the finger-like extensions 824 and 826 snap back to their original position, securing the pen 822 in place. A plurality of vents, 828, are used to allow for release substances, such as heat/steam when the device is sterilized. Adjacent to the recessed area 820, is a second or extended recessed area 830 which contains a securing mechanism, illustrated herein as a compression member 832 which may be used as a compression point for surgical equipment, such as surgical blades stored thereunder.

In addition to the above described features, it is understood that the container 810 may include or be adapted to include one or more features described previously, whether as part of a system or as a feature of a container embodiment including but not limited to monitoring and/or tracking or color coding features.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been described with reference to an example embodiment, it will be understood by those skilled in the art that a variety of modifications, additions and deletions are within the scope of the invention, as defined by the following claims.

What is claimed is:

1. A method for preventing wrong-site surgery and tracking near-miss events as a patient progresses through a surgical procedure environment including a surgeon office, hospital admissions, hospital pre-operative holding area, and an operating room, the method comprising:

identifying a patient in need of a surgical procedure;

creating an electronic patient profile of said patient for use in tracking said patient through said surgical procedure environment, said electronic patient profile including surgical procedure information, patient information, and surgeon information;

associating said electronic patient profile with a container equipped with a machine-readable code containing a unique container identification number and a laterality code, wherein said container includes a surgical instrument for use in said surgical procedure and wherein said electronic patient profile is updated to include said unique container identification number and said laterality code after said electronic patient profile has been associated with said container, said surgical container;

delivering said container to said patient in said hospital pre-operative holding area and tracking said container as said patient progresses through a remainder of said surgical procedure environment;

assessing said electronic patient profile at multiple temporally spaced events within said surgical procedure environment as said patient progresses through said surgical procedure environment to confirm that said electronic patient profile matches with an intended surgical procedure associated with a correct diagnosis of said patient, said intended surgical procedure including a correct patient, a correct procedure, a correct surgical site, and a correct laterality, or does not match with said intended surgical procedure, wherein assessing includes an inspection by a medical team member as to whether said patient information and said surgical procedure information matches said intended surgical procedure and, after said container is delivered to said patient, also includes an electronic scan of said machine-readable code on said container to electronically assess whether said surgical procedure information and said patient information matches said intended surgical procedure, wherein:

if said electronic patient profile matches said intended surgical procedure, allowing said patient to continue to progress within the surgical procedure environment and updating said electronic patient profile to reflect that said electronic patient profile matched said intended surgical procedure, and if said electronic patient profile does not match said intended surgical procedure, at least one of pausing and cancelling the progression of said patient within said surgical procedure environment and updating said electronic patient profile to reflect near-miss data including a mismatch type or reason for said pausing or cancelling of the progression of said patient within said surgical procedure environment; and accessing said container if, during a final assessment of said electronic patient profile in said operating room, it is determined that said electronic patient profile matches said intended surgical procedure such that a surgeon may use said surgical instrument to start said surgical procedure.

2. The method of claim 1, further including the step of providing a final report after said patient has completed their progression within the surgical procedure environment.

3. The method of claim 1, further including the step of associating a visual indicator to said container, said visual indicator providing a user visual confirmation as to a site on said patient where said intended surgical procedure should occur.

4. The method of claim 3, wherein said visual indicator is a color coding, wherein said color indicates a procedure on an anatomical part on the left side, right side, or no lateral side of said patient.

5. The method of claim 1, wherein the step of associating said container with said electronic patient profile of said patient occurs when said patient is scheduled for said intended surgical procedure.

6. The method of claim 1, wherein said machine-readable code is located on a label affixed to said container which when removed from said container permits access to said surgical instrument such that said surgeon may start said surgical procedure.

7. The method of claim 1, including the step of analyzing said near-miss data to determine at least one root cause of said near-miss data.

8. The method of claim 1, further including the step of associating biometric data of said patient with said electronic patient profile.

9. The method of claim 8, wherein said biometric data associated with said electronic patient profile includes at least one of fingerprint data, face recognition data, iris recognition data, retina scan data, and DNA data of said patient.

10. The method of claim 8, further including the steps of:
obtaining said biometric data as said patient progresses within said surgical procedure environment; and
updating said electronic patient profile with said biometric data.

11. The method of claim 1, further including the step of allowing an authorized medical team member to override at least one of said pausing and cancelling the progression of said patient within said surgical procedure environment.

12. The method of claim 1, further including the steps of:
capturing data regarding said patient as said patient progresses through said surgical procedure environment; and
updating said electronic patient profile to include said data captured as said patient progresses within the surgical procedure environment.

13. The method of claim 12, wherein said data is obtained from at least one of a data capture device, a sensor, a wireless data transfer device, and a camera.

14. The method of claim 1, wherein said electronic patient profile includes real-time data obtained from an electronic device capable of recording real-time data, wherein said electronic device includes at least one camera.

15. The method of claim 1, wherein said electronic patient profile is updated to contain a verification that a final timeout has been performed if, during said final assessment of said electronic patient profile in said operating room, it is determined that said electronic patient profile matches said intended surgical procedure.

16. The method of claim 1, wherein said electronic patient profile contains one or more decision input indications that said intended surgical procedure occurred, said intended surgical procedure did not occur, or said intended surgical procedure was paused.

17. The method of claim 1, wherein said electronic patient profile contains a final disposition of said intended surgical procedure, wherein said final disposition includes an indication that a final payment or disbursement of funds occurred.

18. The method of claim 1, wherein said surgical instrument is a surgical blade.

19. The method of claim 1, wherein said machine-readable code is a bar code.

20. The method of claim 19, wherein said bar code is a two-dimensional bar code.

* * * * *

UNITED STATES PATENT AND TRADEMARK OFFICE
CERTIFICATE OF CORRECTION

PATENT NO. : 9,721,064 B2
APPLICATION NO. : 14/873974
DATED : August 1, 2017
INVENTOR(S) : Kaveh Khajavi et al.

It is certified that error appears in the above-identified patent and that said Letters Patent is hereby corrected as shown below:

Column 22, Line 50 for the Claim reference numeral '1', "associated with said container, said surgical container;" should read "associated with said container;"

Signed and Sealed this
Twenty-eighth Day of November, 2017

Joseph Matal
*Performing the Functions and Duties of the
Under Secretary of Commerce for Intellectual Property and
Director of the United States Patent and Trademark Office*